United States Patent
Penner et al.

(10) Patent No.: US 6,431,175 B1
(45) Date of Patent: Aug. 13, 2002

(54) SYSTEM AND METHOD FOR DIRECTING AND MONITORING RADIATION

(75) Inventors: Avi Penner, Tel Aviv; Yariv Porat, Haifa; Eyal Doron, Kiryat Yam, all of (IL)

(73) Assignee: Remon Medical Technologies Ltd., Caesarea (IL)

(*) Notice: Subject to any disclaimer, the term of this patent is extended or adjusted under 35 U.S.C. 154(b) by 0 days.

(21) Appl. No.: 09/305,442

(22) Filed: May 6, 1999

Related U.S. Application Data

(63) Continuation-in-part of application No. 09/000,553, filed on Dec. 30, 1997, now Pat. No. 6,140,740.

(30) Foreign Application Priority Data

Dec. 28, 1998 (WO) ............................... PCT/US98/27669

(51) Int. Cl.⁷ ............................................... A61B 19/00
(52) U.S. Cl. ........................................... 128/899; 600/1
(58) Field of Search ................... 600/1–3; 128/897–99, 128/903

(56) References Cited

U.S. PATENT DOCUMENTS

| | | |
|---|---|---|
| 3,568,661 A | 3/1971 | Franklin |
| 3,757,770 A | 9/1973 | Brayshaw et al. |
| 4,127,110 A | 11/1978 | Bullara |
| 4,227,407 A | 10/1980 | Drost |
| 4,519,401 A | 5/1985 | Ko et al. |
| 4,541,431 A | 9/1985 | Ibrahim et al. |
| 4,593,703 A | 6/1986 | Cosman |
| 4,600,855 A | 7/1986 | Strachan |
| 4,653,508 A | 3/1987 | Cosman |
| 4,660,568 A | 4/1987 | Cosman |
| 4,676,255 A | 6/1987 | Cosman |
| 4,781,715 A | 11/1988 | Wurzel |
| 4,846,191 A | 7/1989 | Brockway et al. |
| 5,024,224 A | 6/1991 | Engebretson |
| 5,178,153 A | 1/1993 | Einzig |
| 5,289,821 A | 3/1994 | Swartz |
| 5,314,457 A | 5/1994 | Jeutter et al. |
| 5,411,551 A | 5/1995 | Winston et al. |
| 5,423,334 A | 6/1995 | Jordan |
| 5,476,488 A | 12/1995 | Morgan et al. |
| 5,562,714 A | 10/1996 | Grevious |
| 5,571,152 A | 11/1996 | Chen et al. |
| 5,628,782 A | 5/1997 | Myers |

(List continued on next page.)

FOREIGN PATENT DOCUMENTS

| | | |
|---|---|---|
| EP | 0897690 A1 | 2/1999 |
| WO | 8303345 A1 | 10/1983 |
| WO | 97/01986 A1 | 1/1997 |
| WO | 97/33513 A1 | 9/1997 |
| WO | 97/47236 A1 | 12/1997 |
| WO | 98/26716 A1 | 6/1998 |
| WO | 98/29030 A1 | 7/1998 |
| WO | 99/26530 A1 | 6/1999 |
| WO | 99/59460 A3 | 11/1999 |
| WO | 99/59460 A2 | 11/1999 |
| WO | 00/16686 A2 | 3/2000 |

OTHER PUBLICATIONS

E.R. Cosman et al (Massachussetts, Apr. 1979) "A Telemetric Pressure Sensor for Ventricular Shunt Systems" Surgical Neurology, vol. 11, No. 4, pp. 287–294.

(List continued on next page.)

*Primary Examiner*—John P. Lacyk

(57) ABSTRACT

A system for monitoring, directing and controlling the dose of radiation in a medical procedure for irradiating a specific region of a patient's body. In its generic form, the system includes at least one sensor being implantable within, or in proximity to, the specific region of the patient's body, the at least one sensor being for sensing at least one parameter associated with the radiation. The system further includes a relaying device which is in communication with the sensor (s). The relaying device serves for relaying the information outside of the patient's body.

65 Claims, 12 Drawing Sheets

U.S. PATENT DOCUMENTS

| | | | |
|---|---|---|---|
| 5,704,352 | A | 1/1998 | Tremblay et al. |
| 5,733,313 | A | 3/1998 | Barrcras, Sr. et al. |
| 5,735,887 | A | 4/1998 | Barreras, Sr. et al. |
| 5,741,316 | A | 4/1998 | Chen et al. |
| 5,804,258 | A | 9/1998 | Cimochowski et al. |
| 5,832,924 | A | 11/1998 | Archibald et al. |
| 5,833,603 | A | 11/1998 | Kovacs et al. |
| 5,843,135 | A | 12/1998 | Weijand et al. |
| 5,873,835 | A | 2/1999 | Hastings et al. |
| 5,957,950 | A | 9/1999 | Mockros et al. |
| 5,967,986 | A | 10/1999 | Cimochowski et al. |
| 6,053,873 | A | 4/2000 | Govari et al. |
| 6,179,767 | B1 * | 1/2001 | Zielgler et al. ............... 600/1 |

OTHER PUBLICATIONS

Z. Tang (May 1995) "Data Transmission form an Implantable Biotelemeter by Load–Shift Keying Using Circuit Configuration Modulator" IEEE Transactions on Biomedical Engineering, vol. 42, No. 5, pp 524–528.

Dipl.–Ing Torsten Eggers et al (Germany) "Implantable Telemetric Endosystem (ITES)" IMSAS Institut Fur Mikrosensoren–Aktuatoren Und–Systeme. 2 pp.

T. Chuter et al (Sweden, Jan. 1997) "Aneurysm Pressure following Endovascular Exclusion" Eur. J. Vasc. Endovasc. Surg. vol. 13, pp 85–87.

Prof. Dr. Johannes Zacheja et al (Germany, Sep. 1996) "An Implantable Microsystem for Biomedical Applications" Micro System Technologies 96, pp 717–722.

C. Hierold et al (Germany, 1998) "Implantable Low Power Integrated Pressure Sensor System for Minimal Invasive Telemetric Patient Monitoring" IEEE, pp 568–573.

Dr. Hartmut Runge (Germany, 1998) "Implanted blood pressure sensor reduces risk of infection for patients hospitalized for long–term observation" Siemens Press Release pp 1–2.

Karl E. Richard et al (Germany, Jan. 1999) "First clinical results with a telemetric shunt–integrated ICP–sensor" Neurological Research vol. 21, pp 117–120.

T.A. Cochran et al (1990) "Aortic Aneurysm Abdominal", Current Therapy in Adult Medicine, Fourth Edition.

G. W. H. Schurink et al (1998) "Late Endoleak after Endovascular Therapy for Abdominal Aortic Aneurysm" Eur. J. Vasc. Endovasc. Surg. vol. 17, pp 448–450.

GH White et al (1997) "Endoleak Following Endoluminal Repair of AAA: Management Options and Patient Outcomes", J. Endovasc Surg. pp. I–45.

S. K. Gupta et al (1999) "Use of a Piezoelectric Film Sensor for Monitoring Vascular Grafts" The American Journal of Surgery vol. 160. pp 182–186.

* cited by examiner

SYSTEM AND METHOD FOR DIRECTING AND MONITORING RADIATION

This is a continuation-in-part of U.S. patent application Ser. No. 09/000,553, filed Dec. 30, 1997, now U.S. Pat. Nos. 6,140,740.

FIELD AND BACKGROUND OF THE INVENTION

The present invention relates to a system and method for intrabody directing and monitoring doses of therapeutic radiation applied to a patient's body. More particularly, the system and method of the present invention employs an implantable sensor coupled to a relaying device, with which, information pertaining to radiation sensed and optionally quantified by the sensors can be relayed outside the body. In addition, the system and method of the present invention can be utilized to assist in directing radiation to a treatment site within the patient's body.

Radiation therapy is used extensively in the medical field to treat a variety of medical conditions. Radiation therapy typically utilizes electromagnetic radiation, typically ionizing radiation, such as, but not limited to, x-ray, gamma-rays and particle beams, as well as ultrasonic radiation to treat many types of cancers, tumors and, cell proliferative disorders as well as non-malignant medical conditions, including, but not limited to, the disintegration of stones.

It will be appreciated that radiation is typically detrimental to living cells. It is known that cancerous cells are more prone to the effects of radiation as such cells are rapidly proliferating cells. However, the effect of radiation on normal cells cannot be overlooked. Thus, when treating with radiation, one desires to apply the maximal possible (optimal) dose onto a specific location, trying, as much as possible to avoid radiating neighboring locations, so as to maximize the treatment vs. injury ratio.

Thus, although with some tumors it is possible to take advantage of the higher sensitivity of the tumor cells to the radiative energy, in most radiation therapy procedures localized treatment is effected by incorporating various methods and devices to direct the radiative beams to the site of treatment, so as to enable radiating at optimal therapeutic doses.

It will be appreciated that the precise aiming and collimating of such radiating beam (several centimeters in diameter) onto the treated site is of prime importance in optimizing the healing/injury ratio (see for example U.S. Pat. No. 3,794,840 to Scott and U.S. Pat. No. 4,995,068 to Chou).

However, in spite of such optimization, in the course of treatment, normal cells which surround the tumorous tissue are also effected by the radiation.

In order to minimize the damage to surrounding healthy tissues several dosage monitoring methods have been utilized by oncologists in conjunction with radiation therapy procedures.

One such monitoring method relies on measuring the entrance and exit doses of radiation. Interpolation of this data is used to determine dosage to tissues. However, measurement of entrance and exit doses combined with interpolation can only predict the dosage of the actual entrance and exit locations which are directly measured. In addition, the dosage applied to the treated locations, where interpolation has been performed, cannot always be predicted from the measured entrance and exit doses.

Another monitoring method involves the surgical implantation of thermoluminescent dosimeter (TLD) devices typically inserted through the midplane of the tumor and in single planes above and below the midplane. Unfortunately, such devices are not designed to relay data outside the patient's body. Thus, not only dosage monitoring is not effected in real time, invasive surgical removal of such devices, under full anesthesia, is required.

Another monitoring method relies on a single skin dose measurement as a checkpoint for the treatment plan. However, this procedure provides the treating physician with very little useful information on the actual dosage delivered deep into the affected tissue and the surrounding body tissues.

Another monitoring method utilized in conjunction with a treatment procedure incorporates a radiation phantom. An example of a radiation phantom is disclosed in U.S. Pat. No. 3,310,885 which describes a radiation phantom for use in a breast irradiation procedure. Such a phantom is fabricated with breast adapters into which TLD devices are inserted, thus, a prescribed radiation treatment is first carried out on the adapter which serves as a control. Although such a system can incorporate many TLD devices and as such, achieve many measurements, the positioning of the adapter, and the size and shape of the adapter is not necessarily repeatable and does not necessarily correspond to the actual positioning, size and shape of the patient's breast and surrounding tissue. A plastic cup strapped to the patient's breast has thus been used to shape the breast of the patient to conform somewhat with the phantom breast adapter. In any case, radiation phantoms are localized outside the patient's body, and as such provide little information, if any, relating to the actual doses applied to the treated site.

Since most of the above mentioned monitoring methods rely heavily on mathematical calculations and projections, such methods fail to accurately predict the doses absorbed by various body regions. Furthermore, since most of these methods employ calculations effected on information retrieved from the dosimetric points, field distortions, which can occur when a radiation beam or beams pass through an organ or tissue are not accounted for.

As such when monitoring is not effected directly in the tumor but rather on the skin, or on an extracorporeal phantom such as with the methods described above, the accurate prediction of dosage to the tumor itself ad to surrounding healthy tissues is not possible.

To try and overcome the limitation inherent to these dosage monitoring methods and as such to try and minimize the damage caused to surrounding healthy tissues while maintaining effective radiation procedure, oncologist often resort to the implantation of radio-opaque metal clips at the tumor boundaries, which can be viewed by a fluoroscope, and as such assist the oncologist to pinpoint the radiation beam.

This method has very poor resolution, does not yield the dose locally absorbed by any specified organ and does not enable a closed loop control of the radiation conditions.

A more precise method for monitoring dosage at a specific treatment site is termed brachytherapy and involves surgically locating a radioactive source in the specific treatment site. Examples of brachytherpy include the implantation of radioactive capsules for a short time period into the cancerous prostate, breast, or brain. Such radioactive capsules are removed following the radiation therapy procedure. There is no control over the local dose and zone of radiation and only remote sensors and indirect calculations are used in order to provide information about the physical properties monitored, as such, the physician has to decide upon the success or damage of the treatment using semi-accurate data. Also, to obtain satisfactory clinical results, such as necrosis of the tumor, a very precise administration of the radioactive source should be kept.

To further increase the accuracy of the irradiation treatment and as such to minimize the damage inflicted upon surrounding healthy tissues several and more advanced systems and methods are utilized.

In treating some cell proliferative disorders it is possible to utilize a microsurgical spot-like radiation beam. This irradiation method allows the oncologist to precisely irradiate small and specific body sections formerly treated by brachytherapy or surgery. One such procedure incorporates what is known in the art as a gamma knife which can be operated on a tumor (in the brain for example), a blood vessel, (such as a coronary artery) where it helps in preventing cell proliferation and restenosis following balloon, stent or graft angioplasty. In a gamma knife procedure, a plurality of gamma radiation beams are directed so as to cross one another at the treatment site, so as to increase the radiative dose thereat, while, at the same time, to reduce the damage to surrounding tissues.

Yet another irradiation procedure which is used for the extermination of malignant cells of a cancerous tumor employs a highly focused microwave beam. An abnormally enlarged or cancerous prostate, breast tumors and some types brain cancer qualify for this type of treatment. The desired destruction is achieved by thermalablation or hyperthermia of the relevant tissue (see, for example, U.S. Pat. No. 5,807,395 to Peter Mulier).

Both the gamma knife and the highly focused microwave beam procedures are advantageous in being non-invasive, but control measurements must be employed against tissue overheating, overexposure or deviation of the beam(s) which may result in damage to the surrounding healthy tissues. In addition, while using microwave radiation a secondary effect caused by the tissue heating resultant from the procedure is a structural modification of the tissue which can lead to a change of the path previously set for the therapeutic radiation.

Although x-ray fluoroscopy is used in combination with these procedures to direct the physician to the site of treatment, this method is limited to stationary treatment sites and as such the application of a gamma knife or a highly focused microwave beam to a treatment site of moving organs such as a pulsating heart cannot be easily effected with accuracy.

In a limited number of medical procedures which incorporate stent or grafts a radioactive source can be incorporated into the stent or graft to effect treatment. Such a radioactive stent or graft typically has a short radiation half-life period which is comparable with the time period corresponding to the cell proliferation stage. Such a device is, therefore, usable only for a very short time period and has a very short shelf life before use. In most cases, it is generally necessary to supplement this procedure with an invasive guide wire catheter procedure which employs a radioactive distal end and inserted within the body for several hours. Moreover, the implantation of a radioactive stent or graft requires both an oncologist and a cardiologist to be present at the time of the procedure further complicating matters.

Thus, there exists no efficient system or method with which a physician can precisely direct a radiation dose of any radiation type to a treatment site and/or monitor with accuracy the radiative dosages absorbed by both the treatment site and the tissue which surrounds the treatment site.

There is thus a widely recognized need for, and it would be highly advantageous to have, a system and method for directing and monitoring a therapeutic radiation dose within a patient's body devoid of the above limitations.

SUMMARY OF THE INVENTION

According to one aspect of the present invention there is provided a system for use in a medical procedure, the medical procedure utilizes radiation for irradiating a specific region of a patient's body, the system comprising (a) at least one sensor being implantable within, or in proximity to, the specific region of the patient's body, the at least one sensor being for sensing at least one parameter associated with the radiation; and (b) a relaying device being in communication with the at least one sensor, the relaying device being for relaying information pertaining to the at least one parameter and therefore to the radiation outside of the patient's body.

According to further features in preferred embodiments of the invention described below, the system further comprising an extracorporeal monitoring unit communicating with the at least one sensor via the relaying device, the relaying device including wires wirable between the at least one sensor and the extracorporeal monitoring unit.

According to still further features in the described preferred embodiments the relaying device further includes a processor communicating with the at least one sensor.

According to still further features in the described preferred embodiments the processor is intrabody transplantable.

According to still further features in the described preferred embodiments the processor is extracorporeal According to still further features in the described preferred embodiments the relaying device is an implantable telemetry device.

According to still further features in the described preferred embodiments the implantable telemetry device includes a processor communicating with the at least one sensor.

According to still further features in the described preferred embodiments the system further comprising an extracorporeal monitoring unit telemetrically communicating with the at least one sensor via the implantable telemetry device.

According to still further features in the described preferred embodiments the system further comprising an extracorporeal monitoring unit telemetrically bidirectionally communicating with the transducer unit via the interrogating signal and the signal receivable outside the body.

According to still further features in the described preferred embodiments the at least one sensor is battery powered and further wherein the relaying device includes a transmitter for relaying information pertaining to the at least one sensor outside the body.

According to still further features in the described preferred embodiments the extracorporeal monitoring unit includes a radiation control feedback element, the radiation control feedback element communicating with a source of the radiation for directing the radiation in a desired direction relative to the at least one sensor.

According to still further features in the described preferred embodiments the extracorporeal monitoring unit includes a radiation dose control feedback element, the radiation dose control feedback element communicating with a source of the radiation for controlling a radiation dose applied to the specific region of the patient's body According to still further features in the described preferred embodiments and as further detailed hereinunder, the at least one sensor is integrated into a stent or graft.

According to another aspect of the present invention, in a medical procedure utilizing radiation for irradiating a specific region of a patient's body, there is provided a method of monitoring the radiation comprising the steps of (a) implanting at least one sensor within, or in proximity to, the specific region of the patient's body, the at least one sensor being for sensing at least one parameter associated with the radiation; and (b) relaying outside the patient's body, during the course of the procedure, information pertaining to the at least one parameter.

According to yet another aspect of the present invention, in a medical procedure utilizing radiation for irradiating a specific region of a patient's body, there is provided a method of directing the radiation relative to the specific region of the patient's body, the method comprising the steps of (a) implanting at least one sensor within, or in proximity to, the specific region of the patient's body, the at least one sensor being for sensing at least one parameter associated with the radiation; and (b) providing outside the body a radiation control feedback element communicating with a source of the radiation and with the at least one sensor, the radiation control feedback element serves for directing the radiation in a desired direction relative to the specific region of the patient's body; and (c) relaying, during the course of the procedure, information pertaining to the at least one parameter from the at least one sensor to the radiation control feedback element for effecting the step of directing the radiation in a desired direction relative to the specific region of the patient's body.

According to still another aspect of the present invention, in a medical procedure utilizing radiation for irradiating a specific region of a patient's body, there is provided, a method of controlling a dose of radiation applied to the specific region of the patient's body, the method comprising the steps of (a) implanting at least one sensor within, or in proximity to, the specific region of the patient's body, the at least one sensor being for sensing at least one parameter associated with the radiation; (b) providing outside the body a radiation control feedback element communicating with a source of the radiation and with the at least one sensor, the radiation control feedback element serves for controlling the dose of radiation being applied to the specific region of the patient's body; and (c) relaying, during the course of the procedure, information pertaining to the at least one parameter from the at least one sensor to the radiation control feedback element for effecting the step of controlling the dose of radiation being applied to the specific region of the patient's body.

According to further features in preferred embodiments of the invention described below, the radiation is provided via a radiation source from either the inside or the outside of the patient's body.

According to still further features in the described preferred embodiments the radiation is a light beam provided from inside the patient's body.

According to still further features in the described preferred embodiments the method further comprising the step of processing the information via a processor.

According to still further features in the described preferred embodiments each of the at least one sensor has an identification code associated therewith for identifying each of the at least one sensor.

According to still further features in the described preferred embodiments the step of relaying outside the patient's body, during the course of the procedure, the information pertaining to the at least one parameter is effected by an implantable telemetry device.

According to still further features in the described preferred embodiments the implantable telemetry device includes a processor communicating with the at least one sensor, the processor serves for processing the information.

According to still further features in the described preferred embodiments the step of relaying outside the patient's body, during the course of the procedure, the information pertaining to the at least one parameter is further effected by an extracorporeal monitoring unit communicating with the at least one sensor via the implantable telemetry device.

According to still further features in the described preferred embodiments the implantable telemetry device includes a transducer unit designed for transducing an interrogating signal receivable from outside the body into a first electrical signal for powering the at least one sensor and for receiving a second electrical signal from the at least one sensor, transducing the second signal into a signal receivable outside the body, such that the information pertaining to the at least one parameter is relayable outside the patient's body following the generation of the interrogating signal.

According to still further features in the described preferred embodiments the transducer unit is an acoustic transducer unit, the interrogating signal is an acoustic interrogating signal, and the signal receivable outside the body is an acoustic signal.

According to still further features in the described preferred embodiments the acoustic transducer unit includes (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments the transducer unit is a radio transducer unit, the interrogating signal is a radio interrogating signal, and the signal receivable outside the body is a radio signal.

According to still further features in the described preferred embodiments the at least one sensor and the radio transducer unit are intrabodily wired so as to enable transplanting the radio transducer unit close to the skin, while at the same time transplanting the at least one sensor deeper within the body of the patient.

According to still further features in the described preferred embodiments the interrogating signal is generated by, and the signal receivable outside the body is received by, an extracorporeal monitoring unit telemetrically bidirectionally communicating with the transducer unit.

According to still further features in the described preferred embodiments the medical procedure is selected from the group consisting of gamma knife microsurgery, thrombolysis, stones disintegration, thermalablation and extermination of benign and malignant tumor masses.

According to still further features in the described preferred embodiments the radiation is selected from the group consisting of an ultrasonic radiation and electromagnetic (both nuclear, i.e., ionizing, and wave, e.g., non-ionizing and ionizing) radiation.

According to still further features in the described preferred embodiments the electromagnetic radiation is selected from the group consisting of alpha radiation, beta radiation, gamma radiation, X-ray radiation and neutron radiation.

According to still further features in the described preferred embodiments the electromagnetic radiation is selected from the group consisting of microwave radiation and visible light radiation, ultraviolet radiation and infrared radiation (e.g., near, medium and far infrared).

According to still further features in the described preferred embodiments the medical procedure is employed for treating a medical disorder characterized by abnormal cell proliferation.

According to still further features in the described preferred embodiments the medical disorder is selected from the group consisting of a tumor, a cancer, a thrombus and restenosis.

According to still further features in the described preferred embodiments the at least one sensor is selected from the group consisting of a temperature sensor, such as a thermocouple or thermistor, an electromagnetic radiation sensor, such as a solid-state diode or a scintillating crystal, an acoustic radiation sensor, such as a hydrophone, a light sensor, such as a photodiode and an electromagnetic field sensor, such as a coil.

According to still further features in the described preferred embodiments the at least one parameter is directly associated with the radiation, thereby the at least one sensor directly senses the radiation.

According to still further features in the described preferred embodiments the at least one parameter is indirectly associated with the radiation, thereby the at least one sensor indirectly senses an interaction of the radiation with the body.

According to still further features in the described preferred embodiments the at least one sensor is selected from the group consisting of a scintillation crystal sensor and a solid state semi-conductor sensor.

According to still further features. in the described preferred embodiments the step of relaying outside the patient's body, during the course of the procedure, the information pertaining to the at least one parameter is effected by a transmitter.

According to an additional aspect of the present invention there is provided an implantable stent or graft system for monitoring, directing and/or dosing radiation applied to a specific region of a patient's body, the stent or graft system comprising (a) a stent or a graft element; (b) at least one sensor being attached to the stent or graft element, the at least one sensor being for sensing at least one parameter associated with the radiation; and (c) a telemetry device being attached to the stent or graft element and being in communication with the at least one sensor, the telemetry device being for relaying the information outside of the patient's body.

According to further features in preferred embodiments of the invention described below, the stent or graft is a vascular stent or graft.

According to still further features in the described preferred embodiments the telemetry device is an acoustic telemetry device.

According to still further features in the described preferred embodiments the telemetry device is a radio frequency telemetry device.

According to still further features in the described preferred embodiments the radiation is selected from the group consisting of an ultrasonic radiation and electromagnetic radiation.

According to still further features in the described preferred embodiments the electromagnetic radiation is selected from the group consisting of alpha radiation, beta radiation, gamma radiation, X-ray radiation and neutron radiation.

According to still further features in the described preferred embodiments the at least one sensor is within a wall of the stent or graft element.

According to still further features in the described preferred embodiments the telemetry device is within a wall of the stent or graft element.

According to still further features in the described preferred embodiments the at least one sensor is externally attached to a wall of the stent or graft element.

According to still further features in the described preferred embodiments the telemetry device is externally attached to a wall of the stent or graft element.

According to still further features in the described preferred embodiments the at least one sensor is internally attached to a wall of the stent or graft element.

According to still further features in the described preferred embodiments the telemetry device is internally attached to a wall of the stent or graft element.

The present invention successfully addresses the shortcomings of the presently known configurations by providing a system and method which relays, during a radiation procedure, information related to the radiation from within the body to the outside. Such information is used according to preferred embodiments of the invention to monitor the radiation and to control its dose and/or direction.

BRIEF DESCRIPTION OF THE DRAWINGS

The invention herein described, by way of example only, with reference to the accompanying drawings, wherein:

FIG. 6a is a cross section of a transducer element according to the present invention taken along line C—C in FIG. 5a;

FIG. 6b is a cross section of a transducer element according to the present invention taken along line D—D in FIG. 5a;

FIG. 6c is a cross section of a transducer element according to the present invention taken along line E—E in FIG. 5a;

FIG. 6d is a cross section of a transducer element according to the present invention taken along line F—F in FIG. 5a;

FIG. 6e is a cross section of a transducer element according to the present invention taken along line G—G in FIG. 5a;

DESCRIPTION OF THE PREFERRED EMBODIMENTS

Figure 1A:
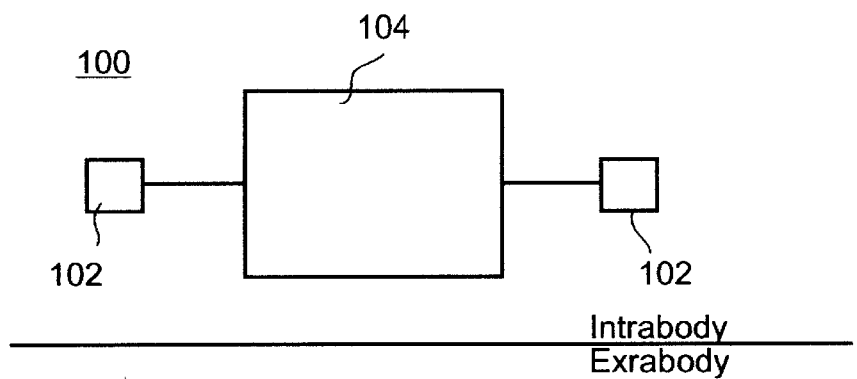
FIGS. 1a–f are block diagrams depicting several configuration of the radiation monitoring system of the present invention.

The present invention is of a system and method which can be used to monitor, control the dose of, and direct, radiation applied to a body of a patient. Specifically, the present invention can be used to relay, outside the body, information pertaining to parameters associated with of radiation, such that the radiation can be precisely directed and the dosage thereof optimized to maximize the healing vs. injury ratio.

The principles and operation of a system and method for intrabody directing and monitoring doses of therapeutic radiation according to the present invention may be better understood with reference to the drawings and accompanying descriptions.

Before explaining at least one embodiment of the invention in detail, it is to be understood that the invention not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1a–f illustrates a system for use in a medical procedure which utilizes radiation for irradiating a specific region of a patient's body, which system is referred to herein as system 100. As further detailed hereinunder, system 100 can be used to monitor, direct and/or control the dose of the radiation applied, to thereby provide effective means to improve the healing to injury ratio.

As shown in FIG. 1a, system 100 includes at least one sensor 102, two sensors 102 are shown. Sensor(s) 102 are implantable within, or in proximity to, the specific region of the patient's body. Sensor(s) 102 serves for sensing at least one parameter associated with the radiation applied to the specific region of the patient's body.

As further shown in FIG. 1a, system 100 further includes a relaying device 104. Device 104 is in communication with sensor(s) 102 and serves for relaying information pertaining to the parameter(s) and therefore to the radiation outside of the patient's body.

As such system 100 can be used to relay, in real time, i.e., in course of the procedure information relating to the radiation applied. Such information can be used according to the present invention and as further detailed hereinunder to control the process of irradiation.

To this end system 100 further includes an extracorporeal monitoring unit 106 which communicates with sensor(s) 102 via relaying device 104.

Figure 1B:
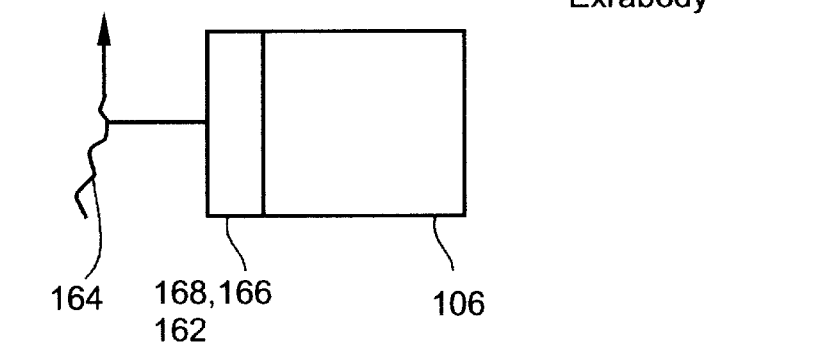
Figure 1B:
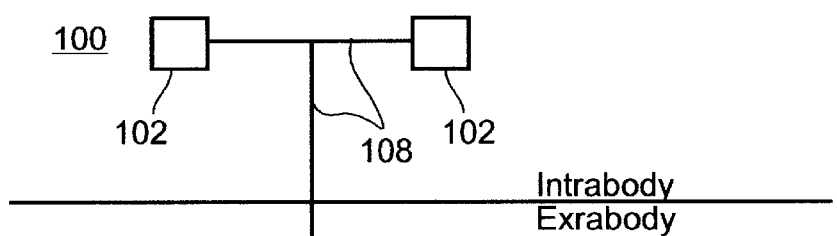

As shown in FIG. 1b, according to one embodiment of the present invention, relaying device 104 (FIG. 1a) is realized as a wires assembly 108, which connects sensor(s) 102 with unit 106. Assembly 108 according to this embodiment serves to (i) power sensor(s) 102 and therefore includes a power source 110; (ii) command sensor(s) 102 and (iii) retrieve information pertaining to the radiation therefrom.

U.S. Pat. No. 4,677,985 which is incorporated herein by reference teaches a wiring assembly communicating with an intracranial pressure sensor and an extracorporeal powering and control unit, which wiring assembly can be employed to implement the present invention.

It will be appreciated that intra-extra body wiring as described has numerous limitations. First, if designed for prolonged implantation such wiring is prone to cause infections. Second, such wiring is complicated to implement especially in cases where sensing of radiation from deep within the body is required.

Thus, according to preferred embodiments of the present invention telemetry is employed to relay the information from sensor(s) 102 outside of the patient's body.

Figure 1C:
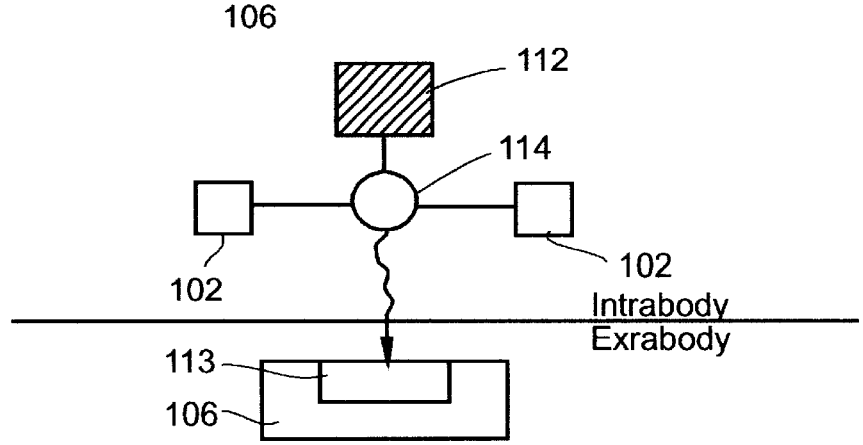

One telemetry base embodiment of the present invention is shown in FIG. 1c, wherein a transmitter 114 communicating with sensor(s) 102 and which is powered by an implantable power source 112, e.g., a battery, or a miniature charged capacitor, is used to transmit the information senses by sensor(s) 102 to a compatible receiver 113 in unit 106. U.S. Pat. Nos. 5,769,877 and 5,807,397, which are incorporated herein by reference, describe implantable, miniature capacitors used as power sources. Receiver 113 and transmitter 114 can be, for example, radio or acoustic transmitter and receiver.

Several methods can be employed to save battery power according to this embodiment of the present invention. In one method, a second set of transmitter and receiver are used to transmit operational command signals from unit 106 to power source 112 and/or sensor(s) 102, to thereby save battery power. In another and similar method, both receiver 113 and transmitter 114 are in effect transceivers which are used both to relay information from sensor(s) 102 to unit 106 and to transmit operational command signals from unit 106 to power source 112 and/or sensor(s) 102, to thereby save battery power. In yet another method, electronics is provided such that sensor(s) 102 are slightly powered at all times (sleep mode), whereas when radiation is sensed thereby, an operational command signal is relayed to power source 112 to provide operational power level (full awake mode), which at the cessation of radiation returns to the sleep mode level, to thereby save power. One ordinarily skilled in the art would be able to devise the required electronics.

It will be appreciated that implantable power source dependent telemetry has limitations inherent to the use of an exhaustible power source. In addition, power sources are space consuming which is less favorable when miniaturization is advantageous, such as in the case of intrabody implanted sensors.

Thus, implantable power source independent telemetry systems are preferably used to implement the present invention as further detailed hereinunder.

As such the intrabody implantable portion of system 100 preferably includes an implantable telemetry device and sensor(s) 102 communicating therewith.

Figure 1D:
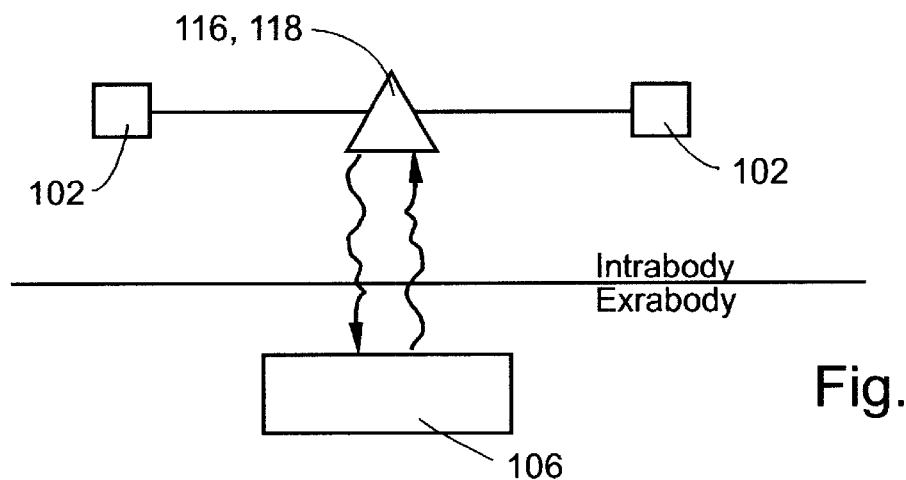

Thus, as shown in FIG. 1*d*, an implantable telemetry device 116 which includes a transducer unit 118 which is designed for transducing an interrogating signal receivable from outside the body into a first electrical signal which serves for powering sensor(s) 102 is employed. Unit 118 according to this embodiment of the present invention further serves for receiving a second electrical signal from sensor(s) 102, transducing the second signal into a signal receivable outside the body by unit 106, such that information pertaining to the radiation is relayable outside the patient's body following generation of interrogating signal by unit 106.

Several designs can be realized to implement this presently most preferred embodiment of the present invention.

Figure 1E:
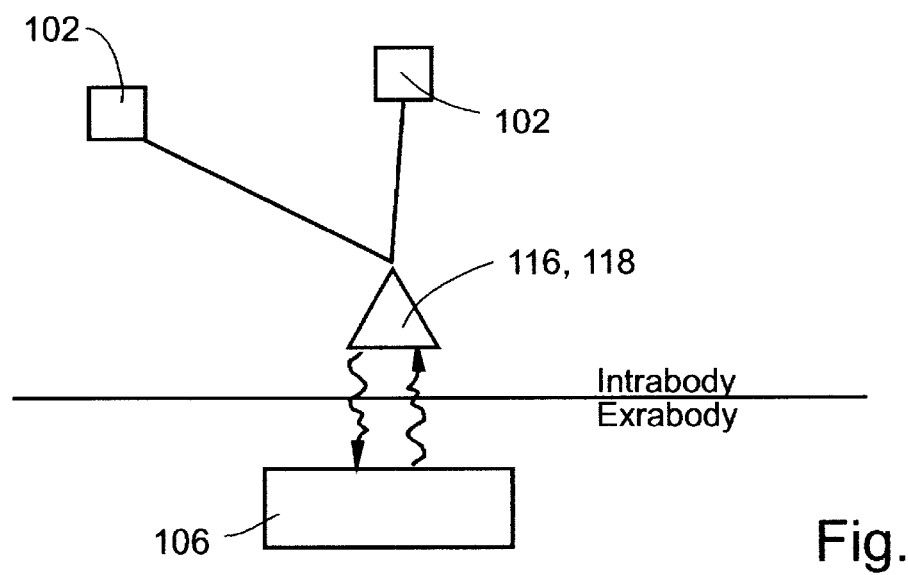

As shown in FIG. 1*e*, according to one configuration transducer unit 118 is a radio frequency transducer unit 118, whereas unit 106 generates a radio frequency interrogating signal carrying sufficient energy to power sensor(s) 102 and to allow unit 118 to relay information relayed thereto from sensor(s) 102 via a return signal receivable by unit 106. It will be appreciated that (i) unit 106 according to this embodiment of the present invention includes a transducer unit with functions in a fashion similar to that of unit 118; and (ii) each of the radio frequency transducer units can include a receiver and a transmitter, or alternatively a transceiver.

According to a preferred embodiment of the present invention radio frequency transducer unit 118 employs Lumped-Constant (L-C) circuits. Transducers incorporating L-C circuits are well known in the art and therefore require no further description herein. For example, U.S. Pat. Nos. 3,943,915 and 4,593,703, which are incorporated herein by reference, teach transducers incorporating L-C circuits which are employed to relay information from an intracranial pressure sensor outside the body of the patient.

It is well known that the signal generatable by an implantable radio frequency transducer is rather weak, necessitating the implantation thereof close to the skin. This however is limitative in case where radiation sensing is required deep within the body because complicated (long) wiring, as shown in FIG. 1*e*, is then required. In an attempt to solve this problem a supplementary power source can be employed with unit 118, subjecting the system to the limitations described above with respect to the use of an implantable power source.

In addition, when using radio frequency telemetry, antenna(s) for receiving/transmitting radio frequency signals should be employed which is cumbersome, space consuming and highly directional dependent.

Figure 1F:
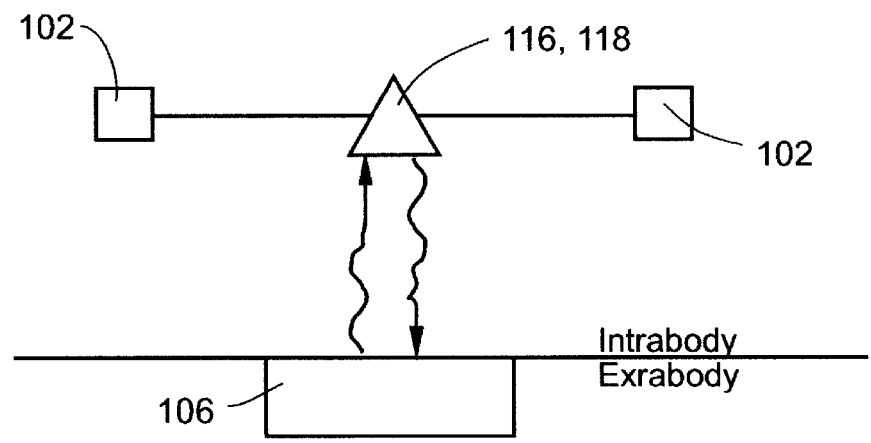

Thus, as shown in FIG. 1*f*, according to another and presently preferred configuration unit 118 is an acoustic transducer unit 118, whereas unit 106 generates an acoustic interrogating signal carrying sufficient energy to power sensor(s) 102 and to allow unit 118 to relay information relayed thereto from sensor(s) 102 via a return signal receivable by unit 106. It will be appreciated that (i) unit 106 according to this embodiment of the present invention includes a transducer unit with functions in a fashion similar to that of unit 118; and (ii) each of the acoustic transducer units can include a receiver and a transmitter, or alternatively a transceiver. The operation of acoustic transducers is described in detail in U.S. patent application Ser. No. 09/000,553, which is incorporated herein by reference and further in the Example section that follows.

The use of acoustic energy to power sensor(s) 102 is specifically advantageous because acoustic energy is readily transmittable with relatively small losses through water bodies such as bodies of living creatures. As a result, the need for transplanting the transducer close to the skin and/or the use of supplementary power source is obviated.

According to another preferred embodiment of the present invention, relaying device 104 also includes a processor. Such a processor can be used to control, modulate and condition the received and the transmitted signals. In addition, the processor can be commanded to condition and route the electrical signal received from sensor(s) 102 so as to enable the retrieval of information from a plurality of sensors 102 utilized by system 100, via a single relaying device 104. Furthermore, and in respect to the battery operated radio frequency transducer mentioned above, the processor can be programmed to minimize the energy expenditure from the battery when system 100 is not operated, and as such to increase the battery life-span.

Thus, according to the present invention, monitoring radiation within, or in close proximity to, a region of a patient's body undergoing a medical procedure utilizing radiation treatment is effected by first implanting sensor(s) 102 within, or in proximity to a treated region of a patient's body. Sensor(s) 102 communicate via physical wires or telemetry with extracorporeal unit 106 through relaying device 104, and optionally with a processor which can be provided within relaying device 104 or preferably within extracorporeal unit 106.

Following implantation, a test run of low dosage radiation, or alternatively a treatment procedure is initiated. Concomitantly with either a test dose, or a treatment dose, sensor(s) 102 are powered by extracorporeal unit 106 to sense parameters indicative of a radiation to which the tissue in which sensor(s) 102 are implanted is exposed to. This information is relayed during the course of the test run, or treatment procedure, from relaying device 104 to extracorporeal unit 106. Relaying is achieved by a signal which can be, depending on relaying device 104, electrical, radio frequency or acoustic. This signal, which carries information pertaining to the radiation to which one or various regions within the patient's body is exposed, is then analyzed by extracorporeal unit 106, and the radiation treatment utilized by the medical procedure is accordingly calibrated or adjusted.

System 100 as so far described can be utilized to monitor radiation so as to enable the physician to (i) manually direct the radiation source to the target by using low dosage and monitoring maximization of the signal received from system 100; (ii) make decisions relating to the duration of treatment; and (iii) manually adjust radiation dosage.

Figure 2:
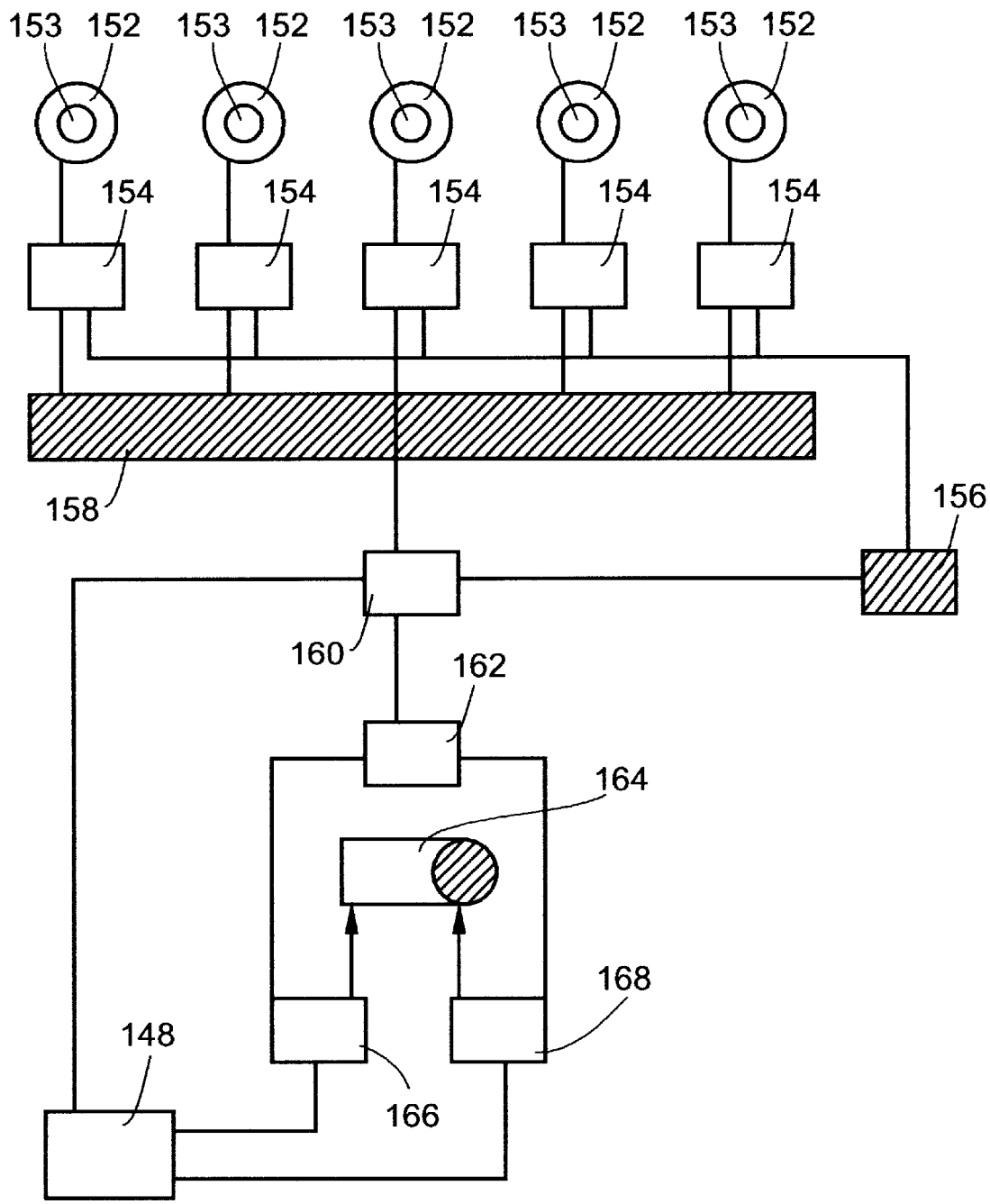
FIG. 2 is a block diagram depicting the components of the extracorporeal monitoring unit employed by the radiation monitoring system of the present invention.

Referring again to FIG. 1*a*, and to FIG. 2, according to another aspect of the present invention system 100 can be effected to automatically adjust the radiation dosage applied to the body of the patient. To this effect, extracorporeal unit 106 of system 100 further includes, a radiation dose control feedback element which includes a feedback control circuit 162 which outputs signals according to the information received from sensor(s) 102 so as to adjust the dosage applied from a radiation source 164 by a dosage adjuster 1681. Preferably, dosage adjustment is performed automatically via dosage adjuster 168 according to information received by extracorporeal unit 106 from sensor(s) 102. Optionally, override control can be effected via user interface 148 which displays the analyzed information received from sensor(s) 102.

Thus, according to this aspect of the present invention, a method of controlling a dose of radiation applied to a specific region of the patient's body is effected by first monitoring radiation as described above. The information relayed during the course of the procedure, or a test run, by sensor(s) 102, is analyzed by extracorporeal unit 106 and used to control via the radiation control feedback element the dosage applied to specific regions within the patient's body.

According to another aspect of the present invention system 100 can be effected to automatically direct the radiation applied to the body of the patient. To this effect, extracorporeal unit 106 of system 100 includes a radiation control feedback element which includes a feedback control circuit 162 which outputs signals according to the information received from sensor(s) 102 so as to adjust the direction of the radiation applied from radiation source 164 by using a radiation directing implement 166. To this end, radiation directing implement 166 is typically a device such as an articulating arm and the like, on which the radiation source is mounted, which controls the positioning of the radiation source with respect to the patient's body. Optionally the position of the body of the patient can also be adjusted, with respect to the radiation source, by manipulating the position of the patient's body. In this case, radiation directing implement 166 can include a mechanism which can be, for example, a spatially orientable bed or surface on which the patient is provided. Still alternatively, and presently preferably, radiation directing implement 166 can include controls for deviating the direction in which the radiation beam is emitted.

One ordinarily skilled in the art would be able to devise and assemble both the radiation dose control feedback element and the radiation direction control feedback element described herein.

Preferably, directing of radiation is performed automatically by radiation directing implement 166 according to information received by extracorporeal unit 106 from sensor (s) 102 and relayed to feedback control circuit 162. Optionally, override control can be effected via user interface 148 which displays the analyzed information received from sensor(s) 102.

Thus, according to this aspect of the present invention, a method of directing the radiation applied to a specific region of the patient's body is effected by first monitoring radiation as described above. The information relayed during the course of the procedure, or during a test run, by sensor(s) 102, is analyzed by extracorporeal unit 106 and used to control through the radiation control feedback element the direction of the radiation applied to the specific region within the patient's body.

Figure 3:
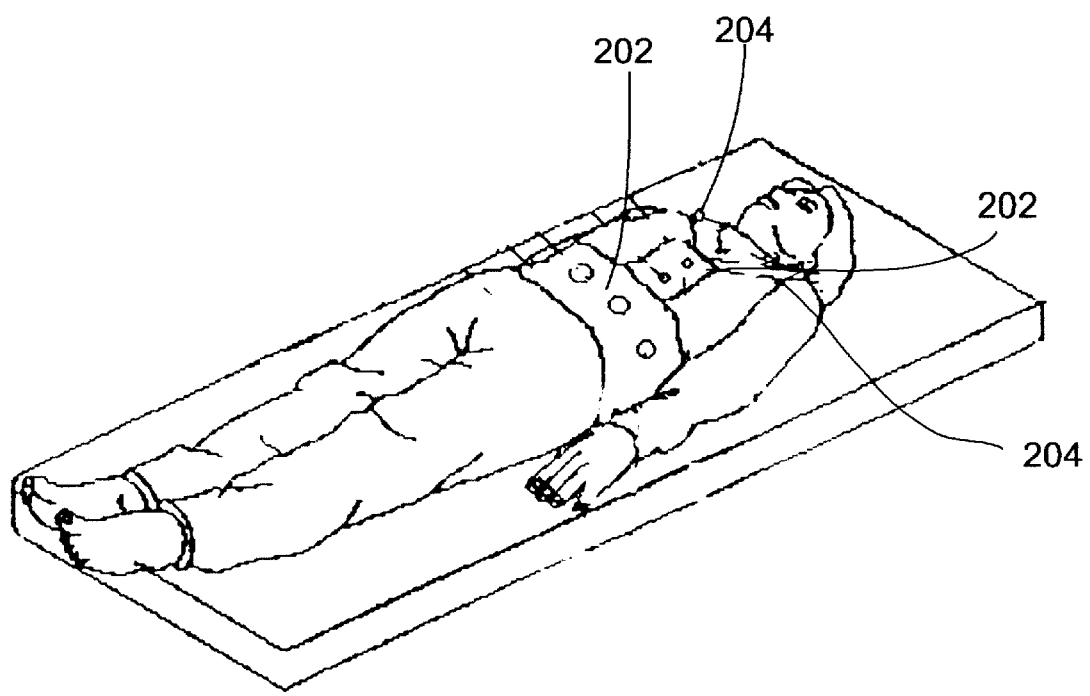
FIG. 3 is a drawing depicting the harness configuration for providing the acoustic transceivers of the extracorporeal monitoring unit in intimate contact with the patient's body.

As further shown in FIGS. 2 and 3, and as already mentioned hereinabove, system 100 includes an extracorporeal monitoring unit 106 communicating with sensor(s) 102 via relaying device 104. To effect communication with relaying device 104, extra corporeal monitoring unit 106 includes extracorporeal relaying devices 152 which are preferably similar to relaying device 104 and thus can be, for example, either electrical contacts or hardwires, or radio frequency or acoustic transducers.

In a presently preferred configuration, and as described hereinabove, devices 152 are similar to telemetry devices 116, and preferably include acoustic transducer units 153 which are similar in construction and operation to acoustic transducer 118 described hereinabove, with the exception that they can transmit a signal of sufficient energy to power sensor(s) 102. As such, couplers 202 which are preferably attached to a harness 204 are used to provide the acoustic transducer of devices 152 in intimate and ordered contact with the patient's body, and as such to ensure optimized energy and data transfer into and out of the patient's body.

According to preferred embodiments of the present invention, each of relaying devices 152 is connected via a separator 154 to a coded power transmitting circuit 156 for relaying a power signal via relaying devices 152 to relaying device 104 which communicate with sensor(s) 102. Relaying devices 152 are further connected to a decoding receiving circuit 158 and a processor 160 with which a received signal is decoded and analyzed for content. In addition, extracorporeal unit 106 also includes a user interface 148 for controlling extracorporeal unit 106 and for communicating and/or presenting analyzed signals to an operator.

As mentioned above, system 100 includes sensor(s) 102 for sensing parameters associated with radiation. Theses parameters can either be directly or indirectly associated with radiation.

To measure direct parameters, sensor 102 can be, for example, an electromagnetic radiation sensor, which can be, but is not limited to, a scintillation crystal sensor or a solid state semi-conductor sensor. An indirect parameter, such as, for example, temperature, which is generated in the tissues upon absorption of some types of radiation, for example, ultrasonic radiation, can be measured via a temperature sensor, such as, but not limited to, a thermocouple or thermistor.

It will be appreciated that many other direct and indirect parameters can be measured and used as an indication of radiation or absorbed radiation. Such parameters can be sensed and measured, for example, by acoustic sensors, electromagnetic sensors and the like. When system 100 employs a plurality of sensors 102, two are shown in FIGS. 1a–f, each sensor is preferably individually coded so as to enable the identification thereof outside the body of the patient. In addition, if a plurality of implantations of the intra body portion of system 100 are implanted within, and in proximity to, the treated region, with each implant including a pair of sensors 102 and a dedicated relaying device 104, then each such implant is preferably also coded, so as to allow the identification of a specific implant in correspondence to the intrabody location thereof.

According to another preferred embodiment of the present invention, the medical procedure which can be monitored and directed by system 100 as herein described can include, but is not limited to, gamma knife microsurgery, thrombolysis, stones disintegration, thermalablation for example, of an enlarged prostate, extermination of benign or malignant tumor masses or the reversal of restenosis. These procedures can employ, for example, electromagnetic, both ionizing and non-ionizing radiation, both particle and wave radiation, such as, but not limited to, gamma radiation, X-ray radiation, alpha radiation, beta radiation, microwave radiation and light radiation, or non-electromagnetic radiation such as ultrasound radiation. Such radiation types are typically employed for destroying a tissue characterized by a cell proliferative disorder, or alternatively, arresting the proliferation of such cells. When disintegrating stones, such as kidney stones or gall bladder stones, radiation, which is typically ultrasound, is used to disintegrate these stones so as to allow their passage out of the body. In this case, monitoring the ultrasonic radiation is only provided for the tissues surrounding the stones such as tissues of the kidney or gall bladder since implantation of system 100 within such stones is neither feasible nor is it necessary.

According to another preferred embodiment of the present invention, when utilizing system 100 with a procedure employing a gamma knife, the principles of which are explained in the background section, the gamma rays can be collimated or directed to cross by information gathered by sensors 102. To effect such collimation, low energy gamma beams or a very short burst of high energy gamma beams can be used test the directionality of radiation emitted by each source. In this case, sensor(s) 102 can be, for example, temperature sensor or preferably radiation sensors. The information retrieved by the extracorporeal unit 106 from sensor(s) 102 can then be used to calibrate the gamma rays in both the directive sense and the dosage sense as further detailed hereinabove.

Figure 4:
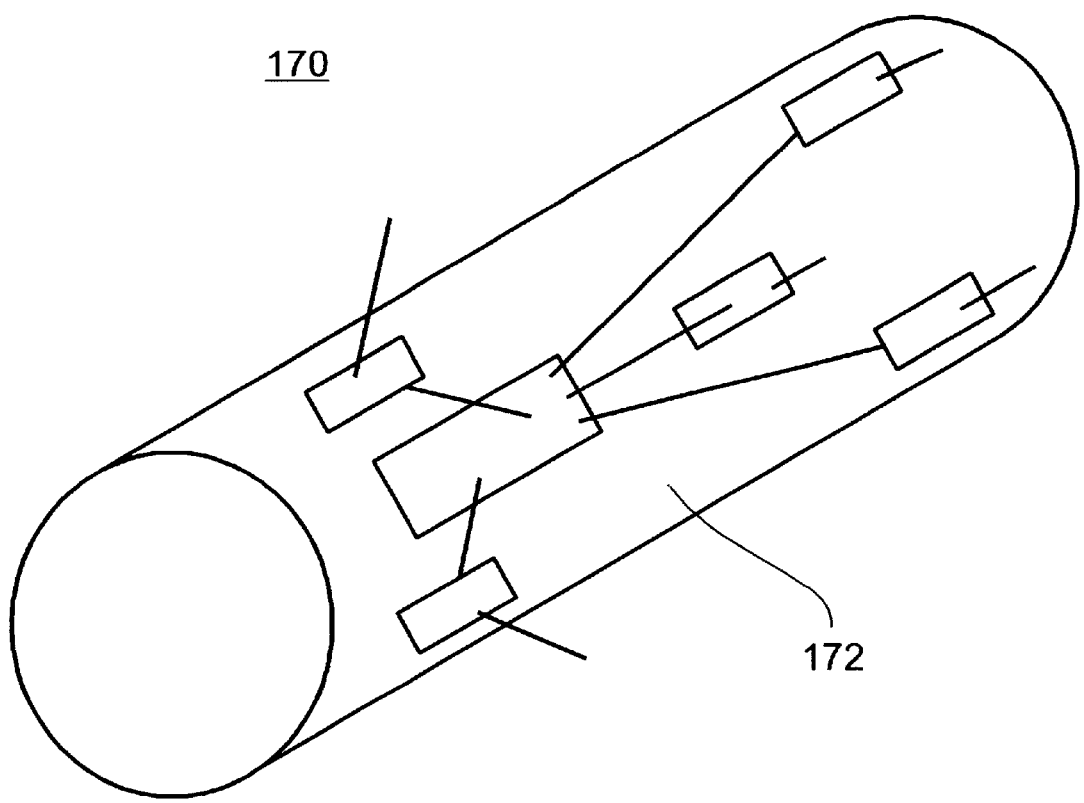
FIG. 4 is a perspective drawing depicting a stent which integrates the monitoring system of the present invention.

According to another aspect of the present invention, and as specifically shown in FIG. 4, sensor(s) 102 and telemetry device 104 are integrated into a vascular stent or graft 170 which is, for example, inserted into an artery following balloon angioplasty, so as to treat restenosis, should restenosis form thereat. Stent or graft 170 includes a plurality of sensors 102 (five are shown) which are externally or internally attached to, or integrated into, a wall 172 thereof. Sensor(s) 102 communicate with telemetry device 116 which is preferably also attached to, or integrated into, wall 172 of stent or graft 170. As such, if, for example, restenosis ensues, radiation therapy can be monitored, dosed and/or directed via stent or graft 170 in a fashion similar to that described hereinabove. In this case, such radiation is utilized to destroy the proliferation of the vascular tissue associated with restenosis.

For system 100 to function properly and efficiently, the implanted sensor(s) 102 and telemetry device 116 including transducer unit 118, which is preferably acoustic, must be miniature in size and convert the power necessary for the various functions thereof from the interrogating signal. As such, the electronic circuitry can be built around existing ultra-low-power microprocessing cores. For example, the implanted portion of system 100 can be constructed around a XE8851 microcontroller with integrated analog-to-digital converter (Xemics SA of Neuchatel, Switzerland). This processor core uses RISC technology, contains integrated ROM and RAM memory, operates on 1.2 V and consumes less than 200 $\mu$A at 1 MHz clock rate, down to less than 30 $\mu$A at 32 kHz clock rate. The surface area of such a processor is just a few mm$^2$.

Using acoustic transducers as transceivers in telemetry device 116 also dramatically reduces the energy requirements of the implanted portion of system 100.

As further detailed in the example section that follows, a plurality of transducer element units, can be made to yield 100–200 $\mu$W of electrical energy arranged on a surface area of 0.8 mm$^2$. Since the requirement of relaying device 104 is no more than a few $\mu$W of acoustic power, which translates into not more than 10–20 $\mu$W of electrical power, the energy requirements can be easily provided by a plurality of transducer element units incorporated into transducer unit 118.

Thus, according to the present invention, a possible device configuration can be for example, a cylindrical structure 2–3 mm in diameter and 3–5 mm in length. Such a structure can easily include the electronic components and at least 20 energy transducer cells, a few of which can double as data transceivers. Such a device is small enough to be implantable in a minimally invasive manner via a standard biopsy needle.

It will be appreciated by one ordinarily skilled in the art that the advantages afforded by the system of the present invention over prior art systems and methods are clearly evident from the above descriptions. By using the system of the present invention a radiation therapy can be calibrated and designed in accordance with real-time and accurate radiation dose monitoring information obtained from inside the body of the patient and from tissue regions which are within, and/or in close proximity to, the treated region. As a result, the system of the present invention can employ direct, real time, and continuous monitoring and as such does not necessitate the incorporation of calculations or projections in order to determine the radiation dose absorbed by the specific tissues of interest.

Furthermore, the present invention can incorporate the monitored information into a system for directing and dosing the radiation, either automatically or manually. Such a feature is not available in the systems currently employed in the art. In addition, since the present invention provides precise means with which radiation can be directed in real-time within the body of a patient, directing of radiation can be effected on both pulsating or moving body organs, and in compensation to the movements of a patient. It will be appreciated that such a feature greatly increases the healing efficacy of the radiation treatment, while at the same time, greatly decreases the chance of inflicting damage to healthy tissues.

Additional objects, advantages, and novel features of the present invention will become apparent to one ordinarily skilled in the art upon examination of the following example, which are not intended to be limiting. Additionally, each of the various embodiments and aspects of the present invention as delineated hereinabove and as claimed in the claims section below finds experimental support in the following examples.

EXAMPLE

Reference is now made to the following example, which together with the above descriptions, illustrate the invention in a non limiting fashion.

For purposes of better understanding the construction and operation of an acoustic transducer utilizable by the system of the present invention, reference is made to the construction and operation of an acoustic transducer as described in U.S. patent application Ser. No. 09/000,553.

Referring again to the drawings, FIGS. 5a, 5b and 6a–6e illustrate a preferred embodiment of a transducer element according to the present invention. As shown in the Figures, a transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit.

The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as KAPTON™ sheets may be used for the production of transducer element 1. Commercially available laminates such as NOVACLAD™ may be used. Alternatively, the substrate may include a silicon layer, or any other suitable material. Alternatively, layer 11 is made of a non-conductive material such as PYRALN™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 $\mu$m. Preferably, the thickness and radius of flexible layer 2, as well as the pressure within cavity 4, are specifically selected so as to provide a predetermined resonant frequency. When using the embodiment of FIGS. 5a and 5b, the radius of layer 2 is defined by the radius of cavity 4.

By using a substantially flexible piezoelectric layer 2, the invention described in U.S. patent application Ser. No. 09/000,553 allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The invention described in U.S. patent application Ser. No. 09/000,553 provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 $\mu$m. Electrically conducting layer 11 preferably has a thickness of about 15 $\mu$m. Cell member 3 is preferably etched completely through the thickness of electrically conducting layer 11. Electrically insulating layer 12 preferably features a thickness of about 50 $\mu$m. The precise dimensions of the various elements of a transducer element according to the invention described in U.S. patent application Ser. No. 09/000,553 may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 6A:
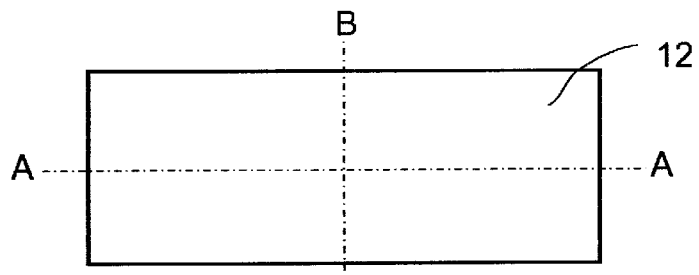
Figure 6B:
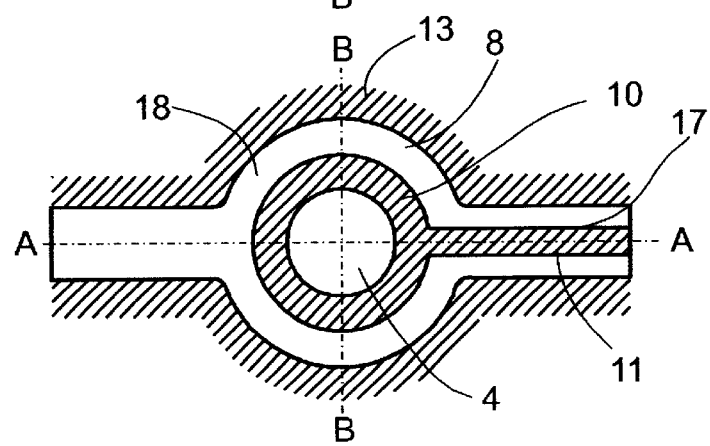

As shown in FIG. 6b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 $\mu$m. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 5A:
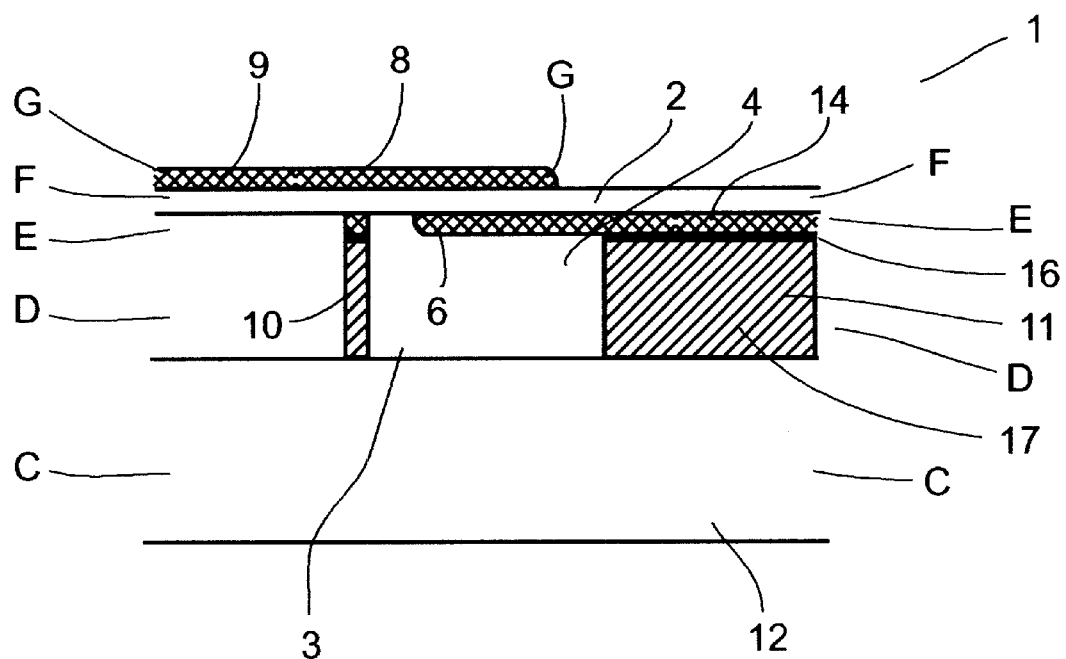
FIG. 5a is a longitudinal section of a transducer element according to the present invention taken along lines A—A in FIGS. 6a–6e.
Figure 5B:
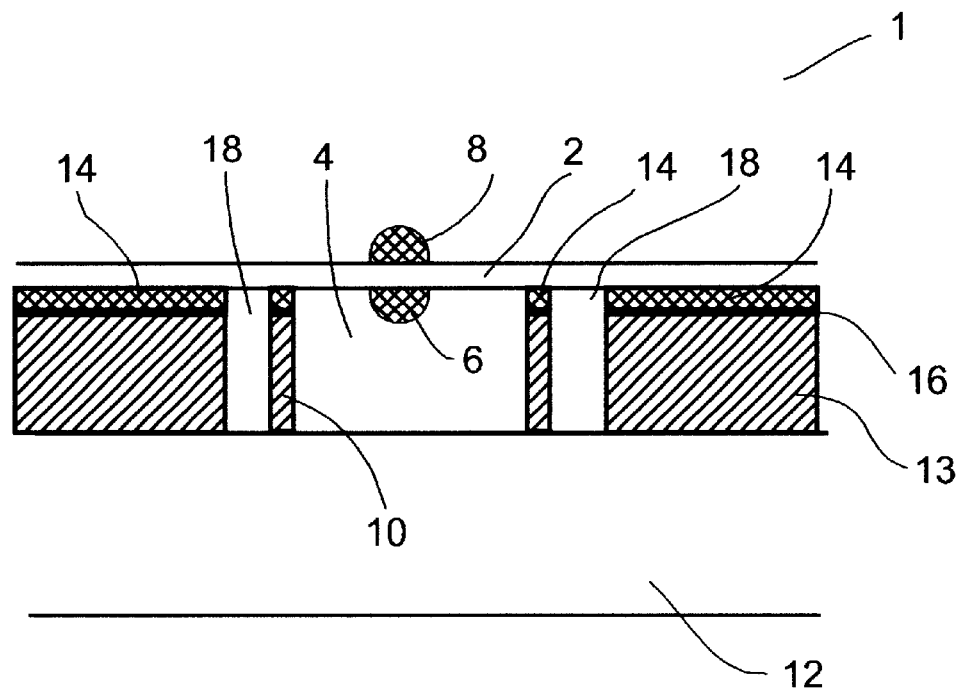
FIG. 5b is a longitudinal section of a transducer element according to the present invention taken along lines B—B in FIGS. 6a–6e.
Figure 6C:
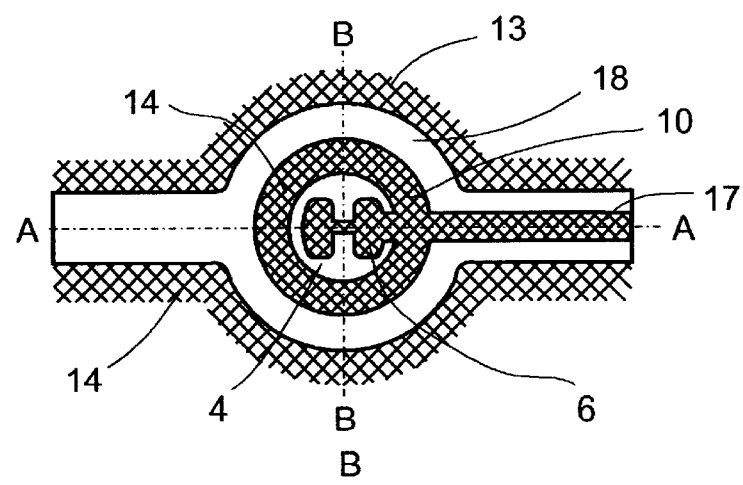
Figure 6D:
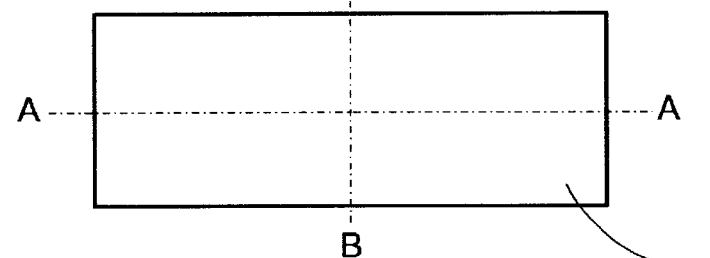
Figure 6E:
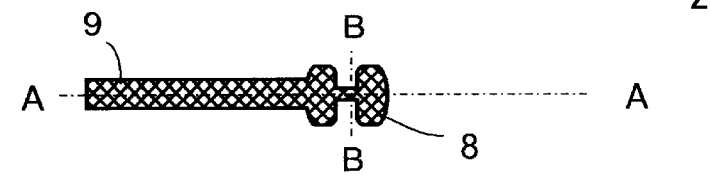

As shown in FIGS. 5a and 5b, attached to piezoelectric layer 2 are upper electrode 8 and lower electrode 6. As shown in FIGS. 6c and 6e, upper electrode 8 and lower electrode 6 are preferably precisely shaped, so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 5a, lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 6c, electrically conducting layer 14 covers the various portions of conducting layer 11, including wall 10 and conducting line 17. The portion of conducting layer 14 covering conducting line 17 is for connection to an electronic component, as further detailed hereinunder.

According to a preferred embodiment, electrodes 6 and 8 are specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; $v$ is the Poisson ratio for layer 2; $\gamma$ is the effective wavenumber in the layer given by: $\gamma^4 = 3\rho(1-v^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r,\varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \quad L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_W a$$

wherein $\Psi(r,\phi)$ is time-dependent and represents the displacement of a selected point located on circular layer 2, the specific location of which is given by radius r and angle $\phi$; J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r,\varphi,t) = \left(e_{31}\left(\frac{\partial\Psi}{\partial x}\right)\right)^2 + \left(e_{32}\left(\frac{\partial\Psi}{\partial y}\right)\right)^2$$

wherein $Q(r,\phi,t)$ represents the charge density at a selected point located on circular layer 2, the specific location of which is given by radius r and angle $\phi$; x is the stretch direction of piezoelectric layer 2; y is the transverse direction (the direction perpendicular to the stretch direction) of layer 2; $e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer. $\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r,\varphi,t)d\vec{x}$$

The capacitance C of piezoelectric layer 2 is given by:

$$C = \frac{\epsilon}{2h}\int_S d\vec{x},$$

wherein $\epsilon$ is the dielectric constant of piezoelectric layer 2; and $2h$ is the thickness of piezoelectric layer 2.

Accordingly, the voltage, current and power responses of piezoelectric layer 2 are evaluated as follows:

$$V = \frac{2h\int_S Q(r,\varphi,t)d\vec{x}}{\epsilon\int_S d\vec{x}}, \quad I = 2i\omega\int_S Q(r,\varphi,t)d\vec{x},$$

$$W = \frac{4ih\left[\int_S Q(r,\varphi,t)d\vec{x}\right]^2}{\epsilon\int_S d\vec{x}}$$

The DC components of Q are usually removed prior to the evaluation, since the DC currents are usually filtered out. The values of Q given above represent peak values of the AC components of Q, and should be modified accordingly, so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 7:
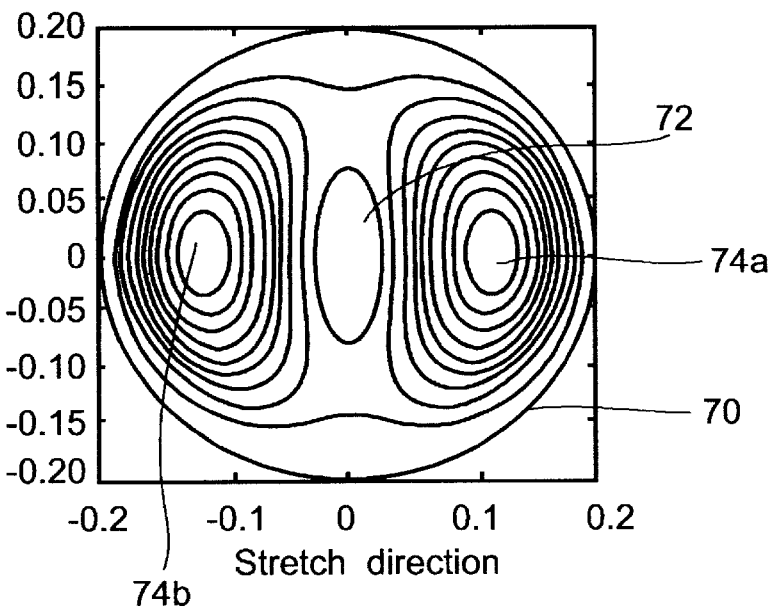
FIG. 7 shows the distribution of charge density across a piezoelectric layer of a transducer element resulting from the application of a constant pressure over the entire surface of the layer.
Figure 8A:
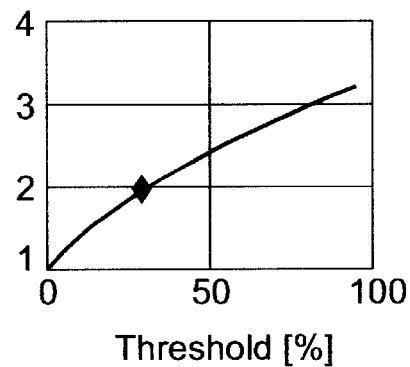
FIG. 8 shows the results of optimization performed for the power response of a transducer according to the present invention.
Figure 8C:
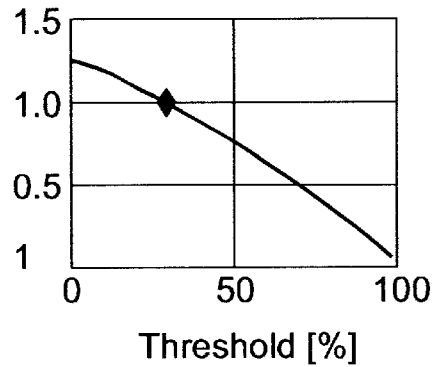
Figure 8B:
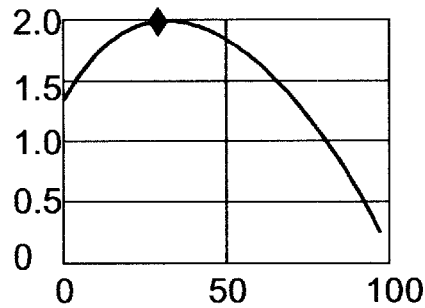
Figure 8D:
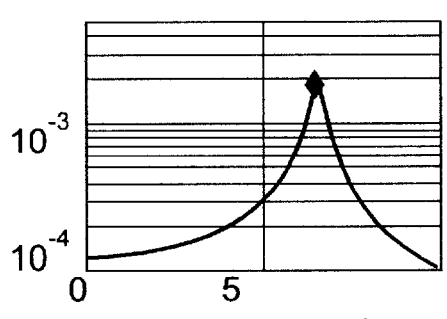

FIG. 7 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 8 shows the results of an optimization performed for the power response of a transducer having a layer 2 of a predetermined area. As shown in the Figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further, as shown in the Figure, the deflection of layer 2 is maximal when applying an acoustic signal at the resonant frequency of layer 2 (graph d).

Figure 9:
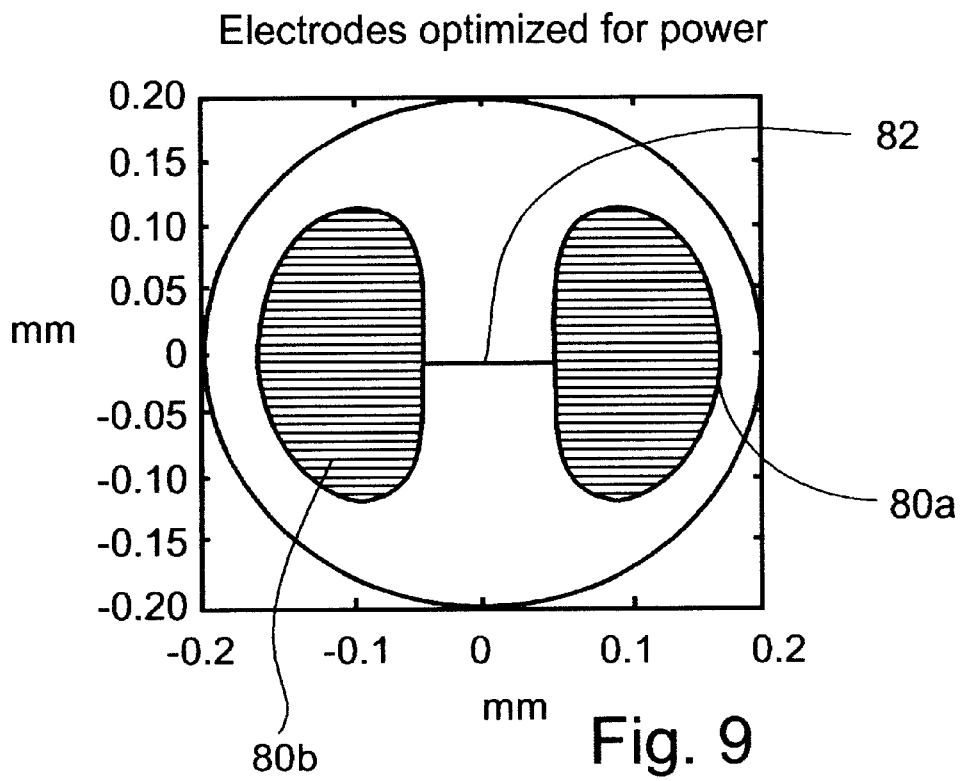
FIG. 9 shows a preferred electrode shape for maximizing the power response of a transducer according to the present invention.

A preferred electrode shape for maximizing the power response of the transducer is shown in FIG. 9, wherein the electrode includes two electrode portions 80a and 80b substantially covering the maximal charge density portions of layer 2, the electrode portions being interconnected by means of a connecting member 82 having a minimal area. Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the invention described in U.S. patent application Ser. No. 09/000,553, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 10:
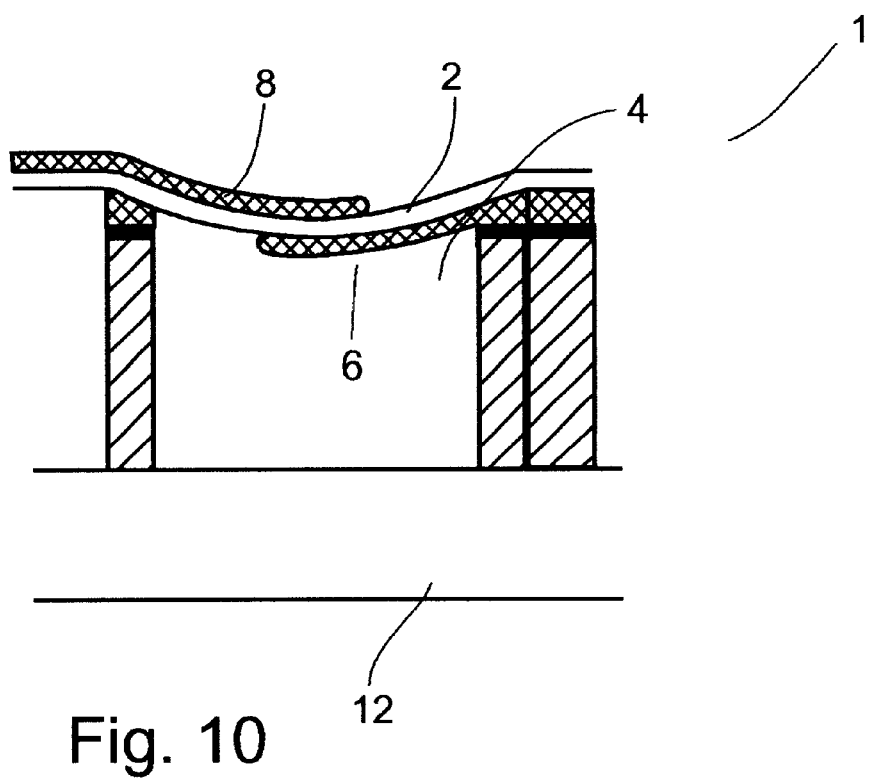
FIG. 10 is a longitudinal section of another embodiment of a transducer element according to the present invention capable of functioning as a transmitter.

Referring now to FIG. 10, according to another embodiment chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P \Psi_{AC} \cos \omega t$, wherein $P_0$ is the static pressure differential between the exterior and the interior of cavity 4; TDC is the displacement resulting from $P_0$; P is the amplitude of the acoustic pressure; and $\Psi_{AC}$ is the displacement resulting from P.

Accordingly, the strain along the x direction includes three terms as follows:

$$S_{xx} = \left(\frac{\partial \Psi}{\partial x}\right)^2 = P_0^2 \left(\frac{\partial \Psi_{DC}}{\partial x}\right)^2 + P^2 \left(\frac{\partial \Psi_{AC}}{\partial x}\right)^2 \cos^2 \omega t + 2 P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment makes it possible to increase the charge output of layer 2 for a given displacement, thereby increasing the voltage, current and power responses of the transducer without having to increase the acoustic pressure P. Furthermore, such embodiment enables to further miniaturize the transducer since the same electrical response may be obtained for smaller acoustic deflections. Such embodiment is substantially more robust mechanically and therefore more durable than the embodiment shown in FIGS. 5a and 5b. Such further miniaturization of the transducer enables to use higher resonance frequencies relative to the embodiment shown in FIGS. 5a and 5b.

Preferably, a transducer element 1 according to the invention described in U.S. patent application Ser. No. 09/000,553 is fabricated by using technologies which are in wide use in the microelectronics industry, so as to allow integration thereof with other conventional electronic components as further detailed hereinunder. When the transducer element includes a substrate such as Copper-polymer laminate or silicon, a variety of conventional electronic components may be fabricated onto the same substrate.

According to a preferred embodiment, a plurality of cavities 4 may be etched into a single substrate 12 and covered by a single piezoelectric layer 2, so as to provide a transducer element including a matrix of transducing cell members 3, thereby providing a larger energy collecting area of predetermined dimensions, while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output o f the transducer.

Furthermore, piezoelectric layer 2 may be completely depolarized and then repolarized at specific regions thereof, so as to provide a predetermined polarity to each of the transducing cell members 3. Such configuration enables to reduce the complexity of interconnections between cell members 3.

A transducer element according to the invention described in U.S. patent application Ser. No. 09/000,553 may be further used as a transmitter for transmitting information to a remote receiver by modulating the reflection of an external impinging acoustic wave arrived from a remote transmitter.

Referring to FIG. 10, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, a specific array of electrodes connected to a single cell member or alternatively to a plurality of cell members are used, so as to control the mechanical impedance of layer 2.

Figure 11A:
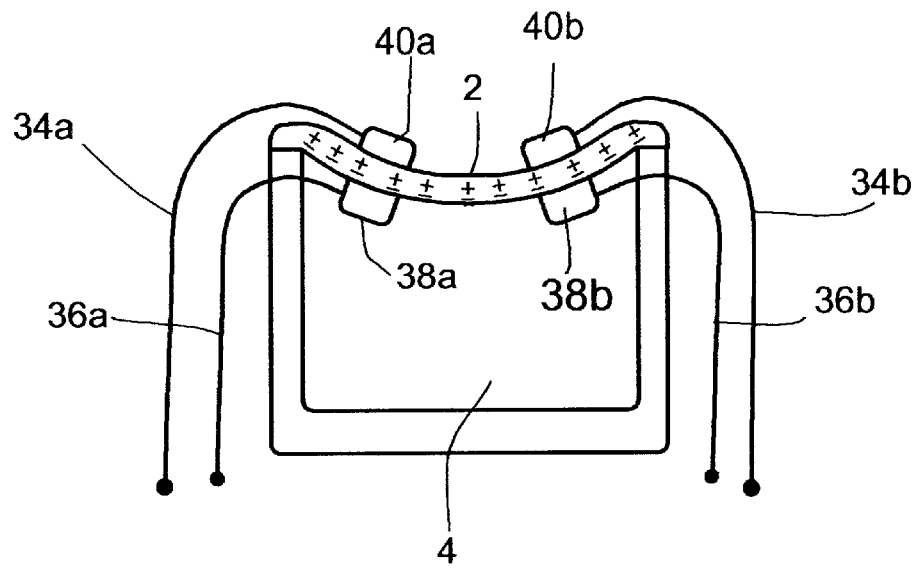
FIGS. 11a–11f are schematic views of possible configurations of transmitters according to the present invention including parallel and anti-parallel electrical connections for controllably changing the mechanical impedance of the piezoelectric layer.

FIGS. 11a–11g illustrate possible configurations for controllably change the impedance of layer 2 of a transmitter element. Referring to FIG. 11a, a transmitter element according to the invention described in U.S. patent application Ser. No. 09/000,553 may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown), so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor as further detailed hereinunder.

Figures 11B, 11C:
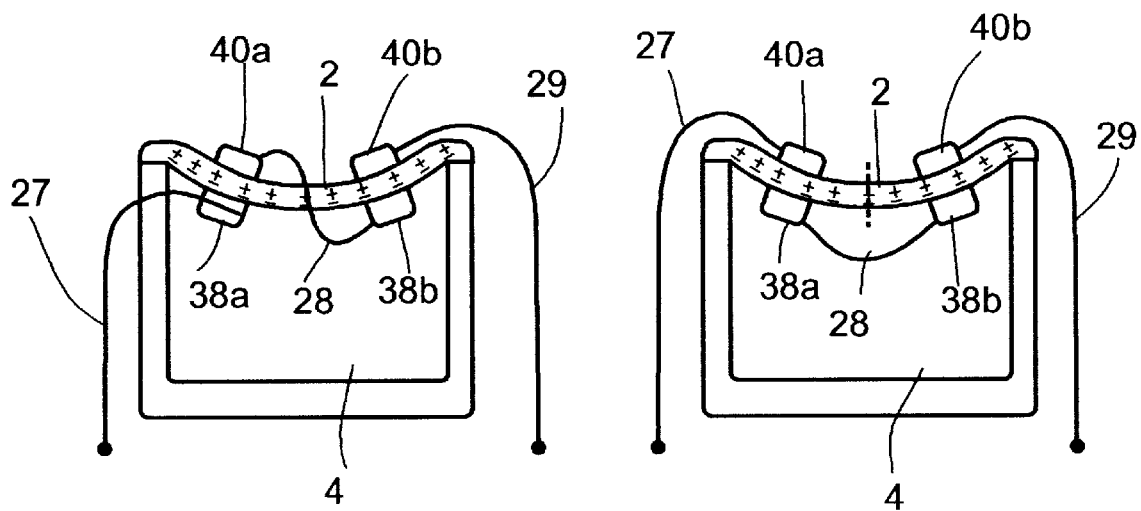

According to another embodiment shown in FIG. 11b, upper electrode 40a is connected to lower electrode 38b by means of a conducting line 28, and electrodes 38a and 40b are connected to an electrical circuit by means of connecting lines 27 and 29, respectively, wherein the electrical circuit further includes a switching element. Such configuration provides an anti-parallel connection of the electrodes, wherein the switching element functions as an on/off switch, thereby alternately increasing the mechanical impedance of layer 2.

In order to reduce the complexity of the electrical connections, layer 2 may be depolarized and then repolarized at specific regions thereof. As shown in FIG. 11c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by means of a conducting line 28, and providing conducting lines 27 and 29 connected to electrodes 40a and 40b, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

Figure 11D:
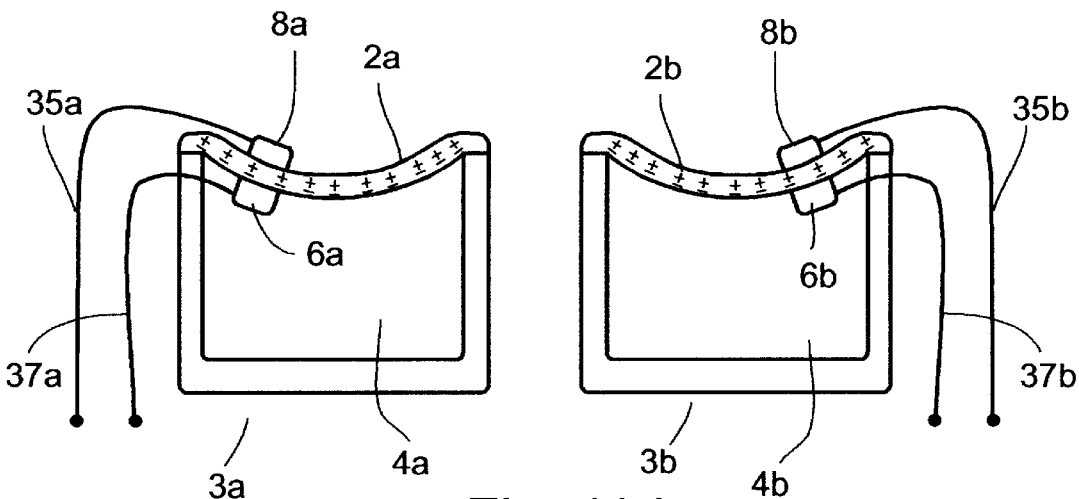

As shown in FIG. 11d, a first transducing cell member 3a including a layer 2a and a cavity 4a, and a second transducing cell member 3b including a layer 2b and a cavity 4b are preferably contained within the same substrate; and layers 2a and 2b are preferably integrally made. A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by means of conducting lines 37a, 35a, 37b and 35b, respectively, the electrical circuit including a switching element, so as to alternately switch the electrical connections of conducting lines 37a, 35a, 37b and 35b, so as to alternately provide parallel and anti-parallel connections, substantially as described for FIG. 11a, thereby alternately decreasing and increasing the mechanical impedance of layers 2a and 2b.

Figure 11E:
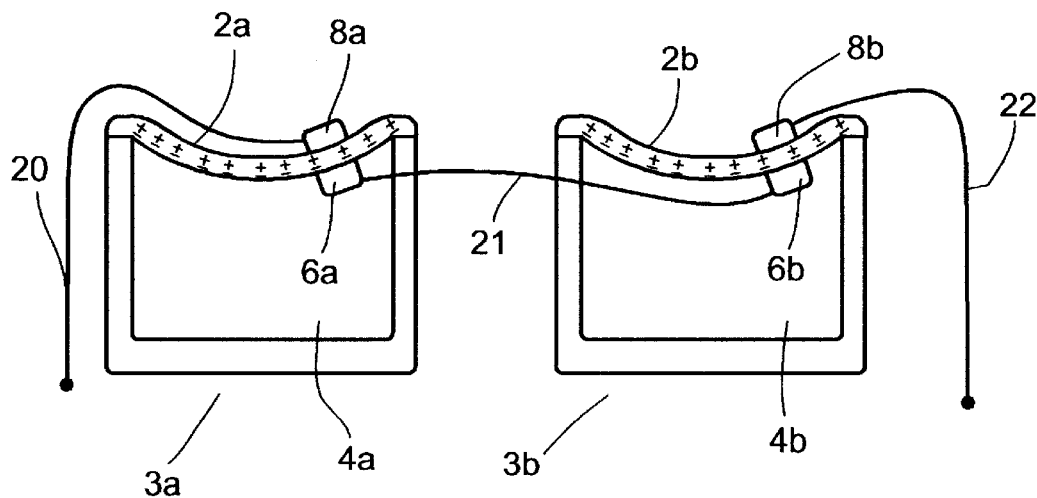

FIG. 11e illustrates another embodiment, wherein the first and second transducing cell members are interconnected by means of an anti-parallel connection. As shown in the Figure, the polarity of layer 2a is opposite to the polarity of layer 2b, so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit which includes a switching element, wherein the switching element preferably functions as an on/off switch, so as to alternately increase the mechanical impedance of layers 2a and 2b.

Figure 11F:
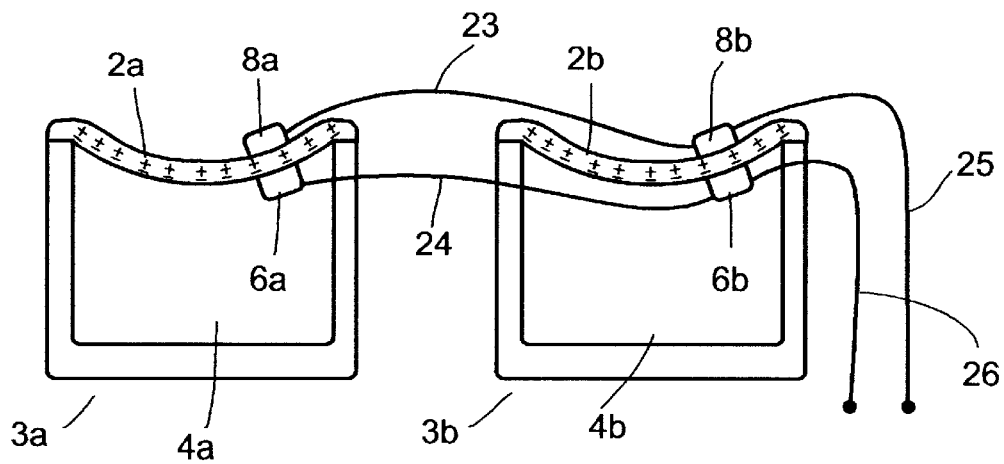

FIG. 11f shows another embodiment, wherein the first and second transducing cell members are interconnected by means of a parallel connection. As shown, electrodes 6a and 6b are interconnected by means of conducting line 24, electrodes 8a and 8b are interconnected by means of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 12:
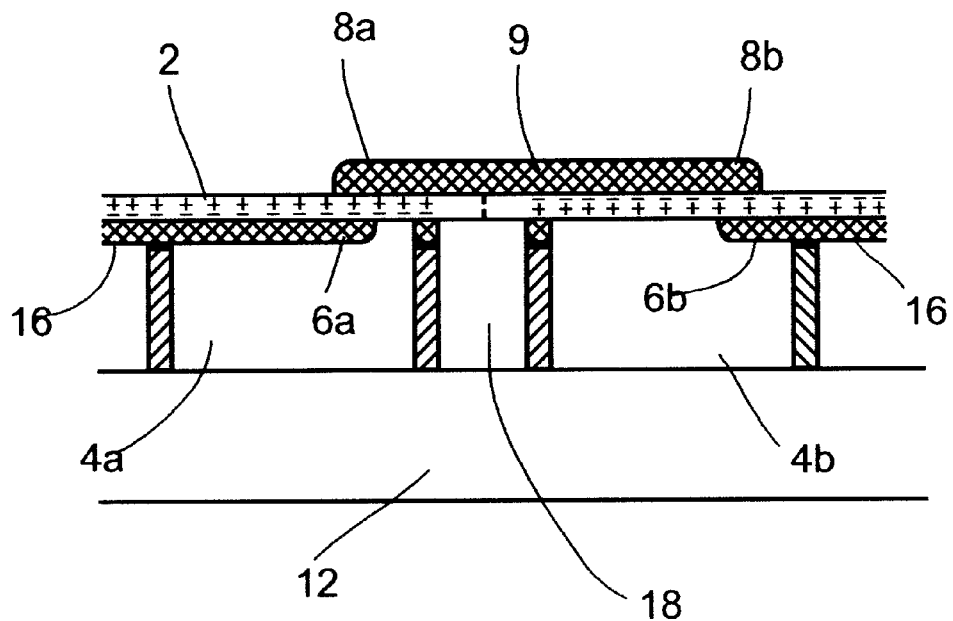
FIG. 12 is a longitudinal section of a transmitter element according to the present invention including an anti-parallel electrical connection.

FIG. 12 shows a possible configuration of two transducing cell members etched onto the same substrate and interconnected by means of an anti-parallel connection. As shown in the Figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by means of a conducting line 9, and electrodes 6a and 6b are provided with conducting lines 16 for connection to an electrical circuit.

Figure 13:
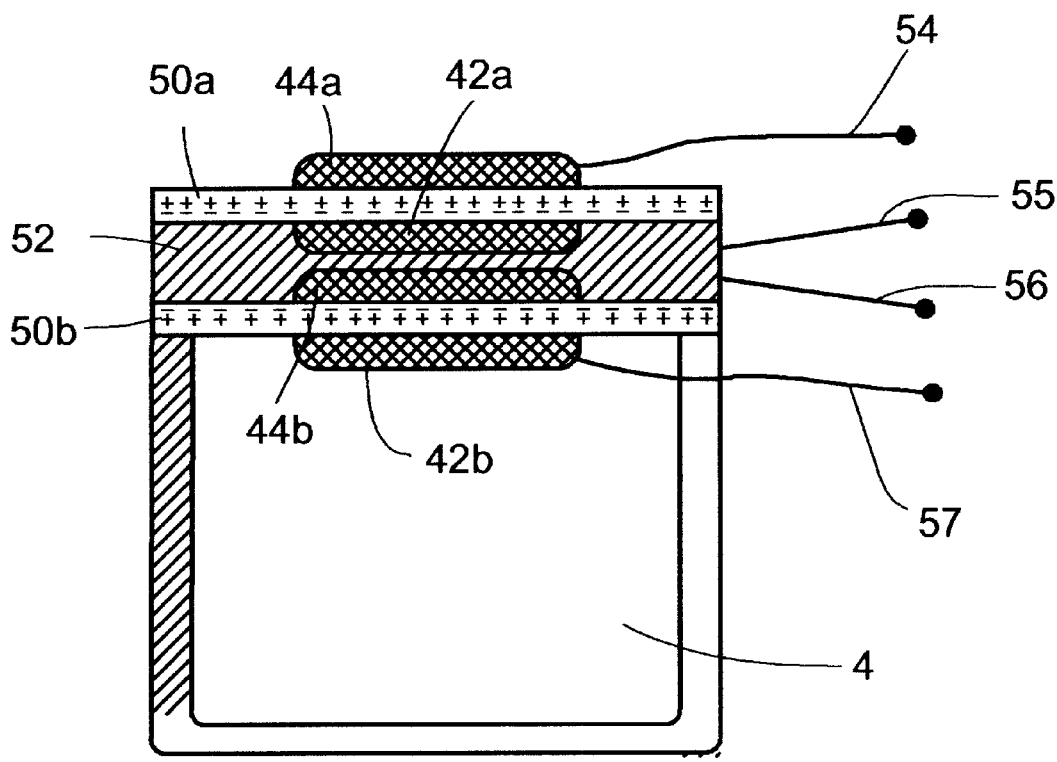
FIG. 13 is a longitudinal section of another embodiment of a transmitter element according to the present invention.

Another embodiment of a transmitter element according to the present invention is shown in FIG. 13. The transmitter element includes a transducing cell member having a cavity 4 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of invention described in U.S. patent application Ser. No. 09/000,553.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A system for use in a medical procedure, said medical procedure utilizes radiation for irradiating a specific region of a patient's body, the system comprising:

(a) at least one sensor adapted to be implanted within, or in proximity to, the specific region of the patient's body, said at least one sensor adapted for sensing at least one parameter associated with the radiation; and (b) a relaying device being in communication with said at least one sensor, said relaying device including a transducer unit designed for transducing an interrogating signal generated outside the body into a first electrical signal for powering said at least one sensor and for receiving a second electrical signal pertaining to said at least one parameter from said at least one sensor and transducing said second electrical signal into a signal transmitted outside the body thereby relaying information pertaining to said at least one parameter and therefore to said radiation outside of the patient's body.

2. The system of claim 1 wherein said relaying device further includes a processor communicating with said at least one sensor.

3. The system of claim 1, wherein each of said at least one sensor has an identification code associated therewith.

4. The system of claim 2, wherein said processor is adapted for intrabody use.

5. The system of claim 2, wherein said processor is adapted for extracorporeal use.

6. The system of claim 1, wherein said relaying device is adapted for intrabody implantation.

7. The system of claim 6, further comprising an extracorporeal monitoring unit telemetrically communicating with said at least one sensor via said implantable telemetry device.

8. The system of claim 1, wherein said transducer unit is an acoustic transducer unit, said interrogating signal is an acoustic interrogating signal, and said signal which can be received outside the body is an acoustic signal.

9. The system of claim 8, wherein said acoustic transducer unit includes:
  (i) a cell member having a cavity;
  (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic; and
  (iii) a first electrode attached to said external surface and a second electrode attached to said internal surface.

10. The system of claim 1, wherein said transducer unit is a radio transducer unit, said interrogating signal is a radio interrogating signal, and said signal which can be received outside the body is a radio signal.

11. The system of claim 10, wherein said at least one sensor and said radio transducer unit are intrabodily wired so as to enable transplanting said radio transducer unit close to the skin, while at the same time transplanting said at least one sensor deeper within the body of the patient.

12. The system of claim 1, further comprising an extracorporeal monitoring unit telemetrically bidirectionally communicating with said transducer unit via said interrogating signal and said signal transmitted outside the body.

13. The system of claim 1, wherein said at least one sensor is adapted for sensing at least one parameter associated with a radiation selected from the group consisting of an ultrasonic radiation and electromagnetic radiation.

14. The system of claim 13, wherein said electromagnetic radiation is selected from the group consisting of alpha radiation, beta radiation, gamma radiation, X-ray radiation and neutron radiation.

15. The system of claim 13, wherein said electromagnetic radiation is selected from the group consisting of microwave radiation, visible light radiation, ultraviolet radiation and infrared radiation.

16. The system of claim 1, wherein said at least one sensor is adapted for sensing at least one parameter associated with a radiation used for treating a medical disorder characterized by abnormal cell proliferation.

17. The system of claim 16, wherein said radiation is used for treating a medical disorder selected from the group consisting of a tumor, a cancer, a thrombus and restenosis.

18. The system of claim 1, wherein said at least one sensor is selected from the group consisting of a temperature sensor, an electromagnetic radiation sensor, an acoustic radiation sensor, a light sensor, and an electromagnetic field sensor.

19. The system of claim 1, wherein said at least one parameter is directly associated with said radiation, thereby said at least one sensor directly senses said radiation.

20. The system of claim 1, wherein said at least one parameter is indirectly associated with said radiation, thereby said at least one sensor indirectly senses an interaction of said radiation with the body.

21. The system of claim 1, wherein said at least one sensor is selected from the group consisting of a scintillation crystal sensor and a solid state semi-conductor sensor.

22. In a medical procedure utilizing radiation for irradiating a specific region of a patient's body, a method of monitoring the radiation comprising the steps of:
  (a) implanting at least one sensor within, or in proximity to, the specific region of the patient's body, said at least one sensor being for sensing at least one parameter associated with the radiation; and
  (b) relaying outside the patient's body, during the course of the procedure, information pertaining to said at least one parameter.

23. The method of claim 22, further comprising the step of processing said information prior to or following step (b).

24. The method of claim 22, further comprising identifying each of said at least one sensor prior to, concomitant with or following step (b).

25. The method of claim 22, wherein the step of relaying outside the patient's body, during the course of the procedure, said information pertaining to said at least one parameter is effected by acoustic or radio transmission.

26. The method of claim 25, wherein step (b) is effected by transducing an interrogating signal generated outside the body into a first electrical signal for powering said at least one sensor and receiving a second electrical signal from said at least one sensor, transducing said second signal into a signal relayed outside the body, said signal including said information pertaining to said at least one parameter.

27. The method of claim 26, wherein said transducing said interrogating signal and said second electrical signal is effected by at least one acoustic transducer unit.

28. The method of claim 27, wherein said at least one acoustic transducer unit includes:
  (i) a cell member having a cavity;
  (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
  (iii) a first electrode attached to said external surface and a second electrode attached to said internal surface.

29. The method of claim 26, wherein said at least one transducer unit is a radio transducer unit, said interrogating signal is a radio interrogating signal, and said signal receivable outside the body is a radio signal.

30. The method of claim 22, wherein said at least one sensor is selected from the group consisting of a temperature sensor, an electromagnetic radiation sensor, an acoustic radiation sensor, a light sensor, and an electromagnetic field sensor.

31. The method of claim 22, wherein said at least one parameter is directly associated with said radiation, thereby said at least one sensor directly senses said radiation.

32. The method of claim 22, wherein said at least one parameter is indirectly associated with said radiation, thereby said at least one sensor indirectly senses an interaction of said radiation with the body.

33. The method of claim 22, wherein said at least one sensor is battery powered and further wherein said step of relaying outside the patient's body, during the course of the procedure, said information pertaining to said at least one parameter is effected by a transmitter.

34. In a medical procedure utilizing radiation for irradiating a specific region of a patient's body, a method of directing the radiation relative to the specific region of the patient's body, the method comprising the steps of:
  (a) implanting at least one sensor within, or in proximity to, the specific region of the patient's body, said at least one sensor being adapted for sensing at least one parameter associated with the radiation; and
  (b) providing outside the body a radiation control feedback element communicating with a source of said radiation and with said at least one sensor, said radiation control feedback element serves for directing said radiation in a desired direction relative to the specific region of the patient's body; and (c) relaying, during the course of the procedure, information pertaining to said at least one parameter from said at least one sensor to said radiation control feedback element for effecting said step of directing said radiation in a desired direction relative to the specific region of the patient's body.

35. The method of claim 34, further comprising the step of processing said information prior to or following step (c).

36. The method of claim 34, further comprising identifying each of said at least one sensor prior to, concomitant with or following step (c).

37. The method of claim 34, further comprising the step of processing said information prior to or following step (c).

38. The method of claim 34, wherein step (c) is effected by transducing an interrogating signal generated outside the body into a first electrical signal for powering said at least one sensor and receiving a second electrical signal from said at least one sensor, transducing said second signal into a signal relayed outside the body, said signal including said information pertaining to said at least one parameter.

39. The method of claim 38, wherein said transducing said interrogating signal and said second electrical signal is effected by at least one acoustic transducer unit.

40. The method of claim 39, wherein said at least one acoustic transducer unit includes:
(i) a cell member having a cavity;
(ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
(iii) a first electrode attached to said external surface and a second electrode attached to said internal surface.

41. The method of claim 38, wherein said at least one transducer unit is a radio transducer unit, said interrogating signal is a radio interrogating signal, and said signal receivable outside the body is a radio signal.

42. The method of claim 34, wherein said at least one sensor is selected from the group consisting of a temperature sensor, an electromagnetic radiation sensor, an acoustic radiation sensor, a light sensor, and an electromagnetic field sensor.

43. The method of claim 34, wherein said at least one parameter is directly associated with said radiation, thereby said at least one sensor directly senses said radiation.

44. The method of claim 34, wherein said at least one parameter is indirectly associated with said radiation, thereby said at least one sensor indirectly senses an interaction of said radiation with the body.

45. The method of claim 34, wherein said at least one sensor is selected from the group consisting of a scintillation crystal sensor and a solid state semi-conductor sensor.

46. The method of claim 34, wherein said at least one sensor is battery powered and further wherein said step of relaying, during the course of the procedure, said information pertaining to said at least one parameter from said at least one sensor to said radiation control feedback element is effected by a transmitter.

47. In a medical procedure utilizing radiation for irradiating a specific region of a patient's body, a method of controlling a dose of radiation applied to the specific region of the patient's body, the method comprising the steps of:
(a) implanting at least one sensor within, or in proximity to, the specific region of the patient's body, said at least one sensor being adapted for sensing at least one parameter associated with the radiation; and
(b) providing outside the body a radiation control feedback element communicating with a source of said radiation and with said at least one sensor, said radiation control feedback element serves for controlling the dose of radiation being applied to the specific region of the patient's body; and
(c) relaying, during the course of the procedure, information pertaining to said at least one parameter from said at least one sensor to said radiation control feedback element for effecting said step of controlling the dose of radiation being applied to the specific region of the patient's body.

48. The method of claim 47, further comprising the step of processing said information prior to or following step (c).

49. The method of claim 47, further comprising identifying each of said at least one sensor prior to, concomitant with or following step (c).

50. The method of claim 47, wherein step (c) is effected by transducing an interrogating signal generated outside the body into a first electrical signal for powering said at least one sensor and receiving a second electrical signal from said at least one sensor, transducing said second signal into a signal relayed outside the body, said signal including said information pertaining to said at least one parameter.

51. The method of claim 50, wherein said transducing said interrogating signal and said second electrical signal is effected by at least one acoustic transducer unit.

52. The method of claim 51, wherein said at least one acoustic transducer unit includes:
(i) a cell member having a cavity;
(ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
(iii) a first electrode attached to said external surface and a second electrode attached to said internal surface.

53. The method of claim 51, wherein said at least one transducer unit is a radio transducer unit, said interrogating signal is a radio interrogating signal, and said signal receivable outside the body is a radio signal.

54. The method of claim 47, wherein said at least one sensor is selected from the group consisting of a temperature sensor, an electromagnetic radiation sensor, an acoustic radiation sensor, a light sensor, and an electromagnetic field sensor.

55. The method of claim 47, wherein said at least one parameter is directly associated with said radiation, thereby said at least one sensor directly senses said radiation.

56. The method of claim 47, wherein said at least one parameter is indirectly associated with said radiation, thereby said at least one sensor indirectly senses an interaction of said radiation with the body.

57. The method of claim 47, wherein said at least one sensor is selected from the group consisting of a scintillation crystal sensor and a solid state semi-conductor sensor.

58. The method of claim 47, wherein said at least one sensor is battery powered and further wherein said step of relaying, during the course of the procedure, said information pertaining to said at least one parameter from said at least one sensor to said radiation control feedback element is effected by a transmitter.

59. A system for use in a medical procedure, said medical procedure utilizes radiation for irradiating a specific region of a patient's body, the system comprising:

(a) at least one sensor being implantable within, or in proximity to, the specific region of the patient's body, said at least one sensor being for sensing at least one parameter associated with the radiation, said at least one sensor having an identification code associated therewith; and (b) a relaying device being in communication with said at least one sensor, said relaying device being for relaying information pertaining to said at least one parameter and therefore to said radiation outside of the patient's body.

60. A system for use in a medical procedure, said medical procedure utilizes radiation for irradiating a specific region of a patient's body, the system comprising:

(a) at least one sensor being implantable within, or in proximity to, the specific region of the patient's body, said at least one sensor being for sensing at least one physiological parameter associated with the radiation; and (b) a relaying device being in communication with said at least one sensor, said relaying device being for relaying information pertaining to said at least one parameter and therefore to said radiation outside of the patient's body.

61. A system for use in a medical procedure, said medical procedure utilizes radiation for irradiating a specific region of a patient's body, the system comprising:

(a) at least one sensor being implantable within, or in proximity to, the specific region of the patient's body, said. at least one sensor being for sensing at least one parameter associated with the radiation;

(b) a power source for powering said at least one sensor to thereby enable sensing said at least one parameter associated with the radiation; and (c) a relaying device being in communication with said at least one sensor, said relaying device being for relaying information pertaining to said at least one parameter and therefore to said radiation outside of the patient's body.

62. A system for use in a medical procedure, said medical procedure utilizes radiation for irradiating a specific region of a patient's body, the system comprising:

(a) at least one sensor being implantable within, or in proximity to, the specific region of the patient's body, said at least one sensor being for sensing at least one parameter associated with the radiation; and (b) a relaying device being in communication with said at least one sensor, said relaying device being for relaying information pertaining to said at least one parameter and therefore to said radiation outside of the patient's body; and (c) an extracorporeal monitoring unit communicating with said relaying device, said extracorporeal monitoring unit serves for receiving information pertaining to said at least one parameter, said extracorporeal monitoring unit including a radiation control feedback element, said radiation control feedback element communicating with a source of the radiation and being for directing the radiation in a desired direction relative to said at least one sensor and/or for controlling a radiation dose applied to the specific region of the patient's body.

63. A implant for use in a medical procedure, the medical procedure utilizing radiation for irradiating a specific region of a patient's body, the implant comprising:

(a) an implant body being adapted for intrabody implantation;

(b) at least one sensor being attached to, or forming a part of said implant body, said at least one sensor being for sensing at least one parameter associated with the radiation; and (c) a relaying device being in communication with said at least one sensor, said relaying device being for relaying information pertaining to said at least one parameter and therefore to said radiation outside of the patient's body.

64. A system for use in a medical procedure, said medical procedure utilizes radiation for irradiating a specific region of a patient's body, the system comprising:

(a) at least one sensor adapted to be implanted within, or in proximity to, the specific region of the patient's body, said at least one sensor adapted for sensing at least one parameter associated with the radiation; and (b) a relaying device being in communication with said at least one sensor, said relaying device including at least one first transducer unit designed for transducing an interrogating signal generated outside the body into a first electrical signal for powering said at least one sensor and at least one second transducer unit for receiving a second electrical signal pertaining to said at least one parameter from said at least one sensor and transducing said second electrical signal into a signal transmitted outside the body thereby relaying information pertaining to said at least one parameter and therefore to said radiation outside of the patient's body.

65. The system of claim 64, wherein said at least one first transducer unit and said at least one second transducer unit are each independently selected from the group consisting of an acoustic transducer unit and an RF transducer unit.

* * * * *